(12) United States Patent
Meech et al.

(10) Patent No.: US 12,702,782 B2
(45) Date of Patent: Aug. 11, 2026

(54) HEADGEAR FOR INFANT RESPIRATORY THERAPY INTERFACE

(71) Applicant: Fisher & Paykel Healthcare Limited, Auckland (NZ)

(72) Inventors: Julio Derek Meech, Auckland (NZ); Freya Refilwe Dixon, Auckland (NZ); Michael Paul Ronayne, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 818 days.

(21) Appl. No.: 17/905,324

(22) PCT Filed: Feb. 25, 2021

(86) PCT No.: PCT/IB2021/051562
§ 371 (c)(1),
(2) Date: Aug. 30, 2022

(87) PCT Pub. No.: WO2021/176305
PCT Pub. Date: Sep. 10, 2021

(65) Prior Publication Data

US 2023/0125759 A1 Apr. 27, 2023

Related U.S. Application Data

(60) Provisional application No. 62/984,158, filed on Mar. 2, 2020.

(51) Int. Cl.
*A61M 16/06* (2006.01)
*A61M 16/08* (2006.01)

(52) U.S. Cl.
CPC .... *A61M 16/0694* (2014.02); *A61M 16/0633* (2014.02); *A61M 16/0688* (2014.02); *A61M 16/0875* (2013.01); *A61M 2205/0216* (2013.01)

(58) Field of Classification Search
CPC .............. A61M 16/06; A61M 16/0605; A61M 16/0616; A61M 16/0633; A61M 16/0683;
(Continued)

(56) References Cited

U.S. PATENT DOCUMENTS 3,442,270 A * 5/1969 Steinman .......... A61F 13/01021 450/154
3,572,329 A 3/1971 De Woskin
(Continued)

FOREIGN PATENT DOCUMENTS

WO WO 2005/076874 A2 8/2005
WO WO 2016/103138 A1 6/2016
(Continued)

OTHER PUBLICATIONS

International Search Report and Written Opinion in PCT application PCT/IB2021/051562 as mailed on Apr. 23, 2021 in 20 pages.

*Primary Examiner* — Annette Dixon
(74) *Attorney, Agent, or Firm* — Knobbe, Martens, Olson & Bear, LLP

(57) ABSTRACT

A patient interface assembly includes a patient interface configured to deliver breathing gases to the airway of a patient. A headgear is configured to support the patient interface on the head of a patient. The headgear can include a tab on each side configured to overlie the patient's cheek and forming a portion or an entirety of an attachment region for the patient interface. The tab can be angled relative to an adjacent portion of the headgear. In some configurations, the headgear includes a rear portion having a first degree of stretch and/or a front portion having a second degree of stretch. In some configurations, the headgear also includes a chinstrap having a third degree of stretch. In some configurations, the third degree of stretch is greater than the first degree of stretch and the second degree of stretch.

20 Claims, 14 Drawing Sheets

(58) Field of Classification Search
CPC .............. A61M 16/0694; A61M 16/08; A61M 16/0816; A61M 16/0825; A61M 16/0841; A61M 2016/0661; A61M 2205/0216; A61M 2205/59; A61M 2207/00; A61M 2210/0618; A62B 18/084; Y10S 128/912; Y10T 29/49826
See application file for complete search history.

(56) References Cited

U.S. PATENT DOCUMENTS 5,662,101 A * 9/1997 Ogden .................. A61M 16/06 128/912
6,119,694 A 9/2000 Correa et al.
6,805,117 B1 * 10/2004 Ho .................... A61M 16/0683 128/207.17
7,779,832 B1 * 8/2010 Ho .................... A61M 16/0683 128/207.17
2003/0145859 A1 * 8/2003 Bohn .................... A61M 16/06 128/206.28
2004/0149280 A1 * 8/2004 Semeniuk ......... A61M 16/0683 128/201.22
2006/0081252 A1 4/2006 Wood
2006/0118119 A1 * 6/2006 Berthon-Jones ...... A61M 16/06 128/206.28
2007/0186931 A1 * 8/2007 Zollinger .......... A61M 16/0683 128/207.11
2009/0211583 A1 * 8/2009 Carroll ................ A62B 18/084 128/207.11
2011/0220113 A1 9/2011 Newman et al.
2014/0305439 A1 * 10/2014 Chodkowski ..... A61M 16/0605 128/207.11
2018/0214654 A1 8/2018 Talbot et al.

FOREIGN PATENT DOCUMENTS

WO WO 2019/111135 A1 6/2019
WO WO 2019/245391 A1 12/2019

* cited by examiner

HEADGEAR FOR INFANT RESPIRATORY THERAPY INTERFACE

BACKGROUND

Field

The present disclosure relates to respiratory interface assemblies. In particular, the present disclosure relates to headgear for respiratory interface assemblies.

Description of Related Art

In assisted breathing, respiratory gases are supplied to a patient through a patient interface via one or more flexible breathing tubes. The patient interface can be a nasal cannula, nasal mask, full face or oro-nasal mask, endotracheal tube, or other known types of interfaces. The patient interface is held in place on the head of the user by a suitable support structure. In some configurations, the patient interface is supported on the user by an adhesive connection with the user's face. However, in other configurations, a headgear arrangement may be preferable for use instead of or in addition to an adhesive connection.

SUMMARY

The systems, methods and devices described herein have innovative aspects, no single one of which is indispensable or solely responsible for their desirable attributes. Without limiting the scope of the claims, some of the advantageous features will now be summarized.

An aspect of the present disclosure involves a headgear for a respiratory interface, including a rear portion having a first degree of stretch, a front portion having a second degree of stretch, and a chinstrap having a third degree of stretch. The third degree of stretch is greater than the first degree of stretch and the second degree of stretch.

In some configurations, the first degree of stretch is substantially non-stretch.

In some configurations, the second degree of stretch is substantially non-stretch.

In some configurations, the third degree of stretch is sufficient to allow a patient to open his or her mouth.

In some configurations, the chinstrap is detachable from one or both of the front portion and the rear portion.

In some configurations, the chinstrap attaches to the front portion.

In some configurations, the chinstrap comprises a first part of a releasable connection and the front portion comprises a second part of the releasable connection, wherein the releasable connection can include but is not limited to a hook and loop fastener, a magnetic fastener, a post and aperture connection, a releasable adhesive, or an interlocking buckle or clip.

In some configurations, the chinstrap is attachable to the front portion such that an effective length of the chinstrap is adjustable.

In some configurations, the chinstrap is a stretch component.

In some configurations, the chinstrap and/or the front portion are configured for attachment to a respiratory interface.

In some configurations, the chinstrap comprises a bifurcated portion, a chin cup and/or a chin gripper configured to be located at a chin of a user.

In some configurations, the front portion is flexible in torsion.

In some configurations, a length of the front portion is adjustable.

In some configurations, the front portion comprises a first strap portion and a second strap portion configured to connect to one another along an overlapping portion, wherein a length of the overlapping portion is variable to permit adjustment of the length of the front portion.

In some configurations, the first strap portion comprises an opening and the second strap portion passes through the opening.

In some configurations, a length of the rear portion is adjustable.

In some configurations, each side of the front portion comprises a buckle, wherein each of a first end and a second end of the rear portion passes through a respective one of the buckles, folds back on itself and attaches to itself.

In some configurations, the rear portion comprises an increased width central portion having a pattern of cutouts.

In some configurations, the pattern of cutouts of the increased width central portion defines a first ellipse and a second ellipse within the first ellipse.

In some configurations, the rear portion comprises a midline strap configured to extend over the top of a head of a user in a forward-rearward direction and attach to the front portion.

In some configurations, the headgear further comprises a notch on each side of the midline strap where the midline strap originates from the rear portion.

In some configurations, the headgear further comprises an attachment region configured to support the respiratory interface.

In some configurations, the attachment region comprises a first part of a releasable connection that is configured to connect to a second part of the releasable connection on the respiratory interface, wherein the releasable connection can include but is not limited to a hook and loop fastener, a magnetic fastener, a post and aperture connection, are leasable adhesive, or an interlocking buckle or clip.

In some configurations, the attachment region comprises a first portion and a second portion, wherein the first portion and the second portion define an angle therebetween.

In some configurations, the angle is between about 110-160 degrees, such as about 140 degrees.

In some configurations, the second portion comprises an attachment tab.

In some configurations, the second portion is configured to be located on the patient's cheek region in use.

An aspect of the present disclosure involves a headgear for a respiratory interface, including a front portion having a first degree of stretch and a chinstrap having a second degree of stretch. The second degree of stretch is greater than the first degree of stretch.

In some configurations, the first degree of stretch is substantially non-stretch.

In some configurations, the second degree of stretch is sufficient to allow a patient to open his or her mouth.

In some configurations, the chinstrap is detachable from the front portion.

In some configurations, the chinstrap comprises a first part of a releasable connection and the front portion comprises a second part of the releasable connection, wherein the releasable connection can include but is not limited to a hook and loop fastener, a magnetic fastener, a post and aperture connection, a releasable adhesive, or an interlocking buckle or clip.

In some configurations, the chinstrap is attachable to the front portion such that an effective length of the chinstrap is adjustable.

In some configurations, the chinstrap is a stretch component.

In some configurations, the chinstrap and/or the front portion are configured for attachment to a respiratory interface.

In some configurations, the chinstrap comprises a bifurcated portion, a chin cup and/or a chin gripper configured to be located at a chin of a user.

In some configurations, the front portion is flexible in torsion.

In some configurations, a length of the front portion is adjustable.

In some configurations, the front portion comprises a first strap portion and a second strap portion configured to connect to one another along an overlapping portion, wherein a length of the overlapping portion is variable to permit adjustment of the length of the front portion.

In some configurations, the first strap portion comprises an opening and the second strap portion passes through the opening.

In some configurations, the headgear includes a rear portion.

In some configurations, the headgear further comprises an attachment region configured to support the respiratory interface.

In some configurations, the attachment region comprises a first part of a releasable connection that is configured to connect to a second part of the releasable connection on the respiratory interface, wherein the releasable connection can include but is not limited to a hook and loop fastener, a magnetic fastener, a post and aperture connection, a releasable adhesive, or an interlocking buckle or clip.

In some configurations, the attachment region comprises a first portion and a second portion, wherein the first portion and the second portion define an angle therebetween.

In some configurations, the angle is between about 110-160 degrees, such as about 140 degrees.

In some configurations, the second portion comprises an attachment tab.

In some configurations, the second portion is configured to be located on the patient's cheek region in use.

An aspect of the present disclosure involves a patient interface assembly including a patient interface configured to deliver breathing gases to the airway of a patient. The patient interface assembly includes a headgear configured to support the patient interface. The headgear includes a chinstrap and a front portion. The patient interface system includes an interface securement system comprising a two-part connection. A first part of the two-part connection is located on the chinstrap or the front portion and a second part of the two-part connection is located on the patient interface.

In some configurations, the patient interface is a sealing interface that contacts and creates a seal with a face of the patient.

In some configurations, the patient interface is a mask or a cannula.

In some configurations, the patient interface comprises a pair of side arms located on opposite sides of a body portion.

In some configurations, the headgear comprises a rear portion.

In some configurations, the front portion is substantially rigid.

In some configurations, the front portion and/or the rear portion are substantially non-stretch.

In some configurations, the chinstrap is a stretch component.

In some configurations, the chinstrap is detachable from another portion or a remainder of the headgear.

In some configurations, the chinstrap comprises a bifurcated portion, a chin cup and/or a chin gripper configured to be located at a chin of a patient.

In some configurations, the first part and the second part of the two-part connection are releasable from one another.

In some configurations, the first part of the two-part connection of the interface securement system comprises a pair of first connection portions, each located on an opposite side of the headgear.

In some configurations, the chinstrap comprises the pair of first connection portions.

In some configurations, the front portion comprises the pair of first connection portions.

In some configurations, the front portion comprises a pair of side tabs located on opposite sides of the front portion, each of the pair of side tabs comprising the first part of the two-part connection to thereby define one of the pair of first connection portions.

In some configurations, the second part of the two-part connection of the interface securement system comprises a pair of second connection portions, each located on an opposite side of the patient interface.

In some configurations, each of the pair of second connection portions are located on a respective one of the pair of side arms of the patient interface.

In some configurations, the two-part connection of the interface securement system can include but is not limited to a hook and loop fastener, a magnetic fastener, a post and aperture connection, a releasable adhesive, or an interlocking buckle or clip.

In some configurations, each of the pair of side tabs defines an angle with an adjacent portion of the headgear.

In some configurations, the angle is between about 110-160 degrees, such as about 140 degrees.

In some configurations, each of the pair of side tabs is configured to be located on the patient's cheek region in use.

In some configurations, the front portion comprises a composite structure of a plastic core and a textile cover, wherein the cover and the core are attached by a permanent bond created by introduction of a molten material onto or into the cover, which is allowed to cool to form the core.

An aspect of the present disclosure involves a patient interface assembly including a patient interface configured to deliver breathing gases to the airway of a patient. The patient interface assembly includes an inspiratory tube configured to deliver the breathing gases to the patient interface. The patient interface assembly includes a headgear configured to support the patient interface. The headgear includes a rear portion having a first degree of stretch and/or a front portion having a second degree of stretch, and a chinstrap having a third degree of stretch. The third degree of stretch is greater than the first degree of stretch and the second degree of stretch.

In some configurations, the first degree of stretch is substantially non-stretch.

In some configurations, the second degree of stretch is substantially non-stretch.

In some configurations, the third degree of stretch is sufficient to allow a patient to open his or her mouth.

In some configurations, the chinstrap is detachable from one or both of the front portion and the rear portion.

In some configurations, the chinstrap attaches to the front portion.

In some configurations, the chinstrap comprises a first part of a releasable connection and the front portion comprises a second part of the releasable connection, wherein the releasable connection can include but is not limited to a hook and loop fastener, a magnetic fastener, a post and aperture connection, a releasable adhesive, or an interlocking buckle or clip.

In some configurations, the chinstrap is attachable to the front portion such that an effective length of the chinstrap is adjustable.

In some configurations, the chinstrap is a stretch component.

In some configurations, the chinstrap and/or the front portion are configured for attachment to the patient interface.

In some configurations, the chinstrap comprises a bifurcated portion, a chin cup and/or a chin gripper configured to be located at a chin of a user.

In some configurations, the front portion is flexible in torsion.

In some configurations, a length of the front portion is adjustable.

In some configurations, the front portion comprises a first strap portion and a second strap portion configured to connect to one another along an overlapping portion, wherein a length of the overlapping portion is variable to permit adjustment of the length of the front portion.

In some configurations, the first strap portion comprises an opening and the second strap portion passes through the opening.

In some configurations, a length of the rear portion is adjustable.

In some configurations, each side of the front portion comprises a buckle, wherein each of a first end and a second end of the rear portion passes through a respective one of the buckles, folds back on itself and attaches to itself.

In some configurations, the rear portion comprises an increased width central portion having a pattern of cutouts.

In some configurations, the pattern of cutouts of the increased width central portion defines a first ellipse and a second ellipse within the first ellipse.

In some configurations, the rear portion comprises a midline strap configured to extend over the top of a head of the patient in a forward-rearward direction and attach to the front portion.

In some configurations, a notch on each side of the midline strap where the midline strap originates from the rear portion.

In some configurations, the patient interface assembly further includes an interface securement system configured to couple the patient interface to the headgear. The interface securement system includes a two-part connection, wherein a first part of the two-part connection is located on the chinstrap or the front portion and a second part of the two-part connection is located on the patient interface.

In some configurations, the patient interface further comprises an expiratory conduit configured to convey expired gases and an unused portion of the breathing gases away from the patient interface.

In some configurations, the expiratory conduit is connected to a resistance device, which can be a water resistance valve.

In some configurations, the patient interface is a sealing interface that contacts and creates a seal with a face of the patient.

In some configurations, the patient interface is a mask or a cannula.

In some configurations, the patient interface comprises a pair of side arms located on opposite sides of a body portion.

In some configurations, the inspiratory tube is attachable to the headgear.

In some configurations, the headgear comprises a loop configured to secure the inspiratory tube relative to the headgear.

In some configurations, the expiratory tube is attachable to the headgear.

In some configurations, the headgear comprises a loop configured to secure the expiratory tube relative to the headgear.

An aspect of the present disclosure involves a headgear for a respiratory interface, which includes a body portion having an attachment region configured to support the respiratory interface. The headgear also includes a chinstrap. The attachment region comprises a first part of a releasable connection that is configured to connect to a second part of the releasable connection on the respiratory interface, wherein the releasable connection can include but is not limited to a hook and loop fastener, a magnetic fastener, a post and aperture connection, a releasable adhesive, or an interlocking buckle or clip.

In some configurations, the body portion comprises a first portion and a second portion, wherein the first portion and the second portion define an angle therebetween and wherein the attachment region is located at least on the second portion.

In some configurations, the angle is between about 110-160 degrees, such as about 140 degrees.

In some configurations, the second portion comprises an attachment tab.

In some configurations, the second portion is configured to be located on the patient's cheek region in use.

In some configurations, the attachment region is located on both of the first portion and the second portion.

In some configurations, the body portion comprises a composite structure of a plastic core and a textile cover, wherein the cover and the core are attached by a permanent bond created by introduction of a molten material onto or into the cover, which is allowed to cool to form the core.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

DETAILED DESCRIPTION

Figure 1:
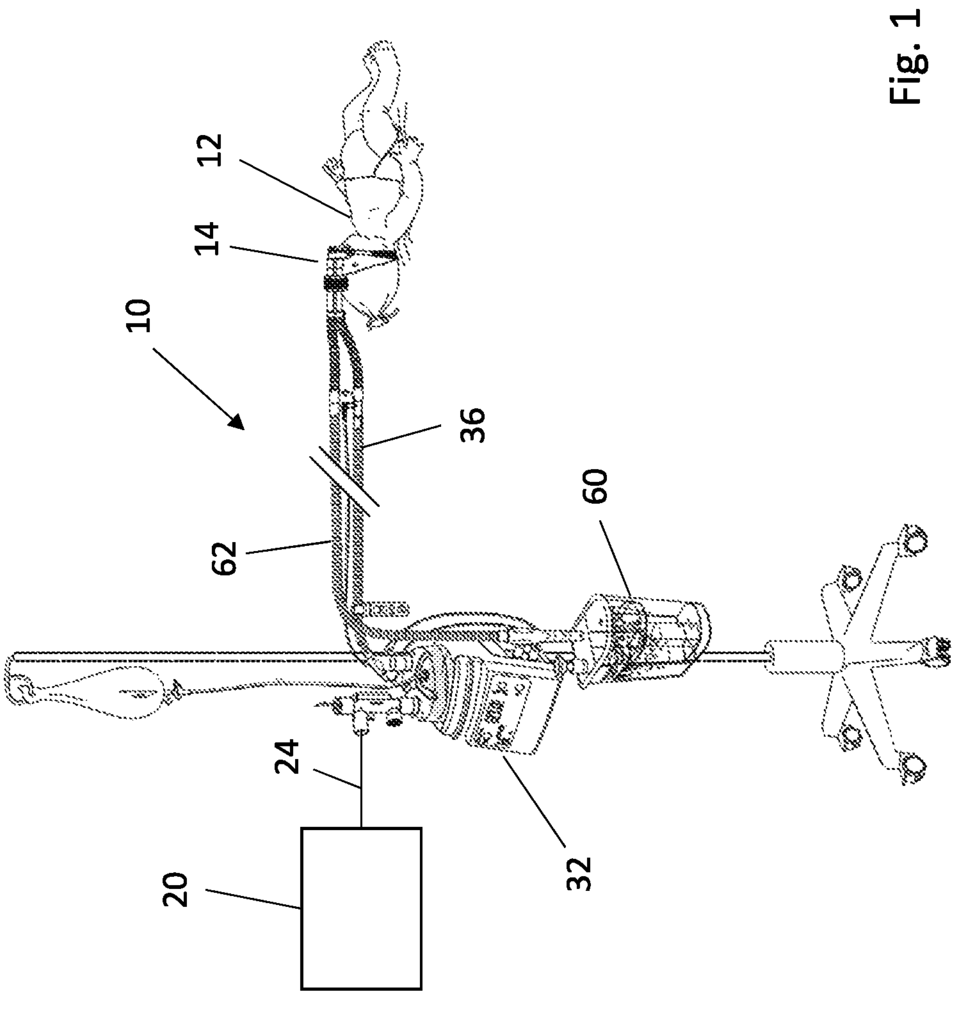
FIG. 1 illustrates an infant patient receiving positive airway pressure (e.g., CPAP) therapy from a system including an inspiratory pressure device, a humidifier, a patient interface and an expiratory pressure device.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as “above” and “below” refer to directions in the drawings to which reference is made. Terms such as “front,” “back,” “left,” “right,” “rear,” and “side” describe the orientation and/or location of portions of the components or elements within a consistent but arbitrary frame of reference which is made clear by reference to the text and the associated drawings describing the components or elements under discussion. Moreover, terms such as “first,” “second,” “third,” and so on may be used to describe separate components. Such terminology may include the words specifically mentioned above, derivatives thereof, and words of similar import.

FIG. 1 illustrates infant positive airway pressure (PAP) (e.g., continuous positive airway pressure (CPAP)) system, generally referred to by the reference numeral 10. The system 10 is capable of providing PAP (e.g., CPAP) therapy to a neonate or an infant patient 12 for an extended period of time. The PAP therapy is delivered through a suitable patient interface 14. The system 10 is disclosed herein in the context of continuous positive airway pressure (CPAP) therapy; however, the system 10 could also provide other types or modes of positive airway pressure (PAP) therapy. Accordingly, references to CPAP therapy herein are understood to also include other types of PAP therapies, unless specifically indicated otherwise.

The illustrated system 10 includes a source of breathing gas, which can be a flow generator 20 that produces a pressurized flow of atmospheric air. However, other suitable sources of breathing gas can also be used. The breathing gas can be air, oxygen, a blend of air and oxygen, or any other suitable gas for use in respiratory therapy. The source of breathing gas provides a flow of breathing gas at an initial pressure or within an initial pressure range. The flow rate of the flow of breathing gas can be provided at a suitable level for the desired therapy.

A first gases supply conduit 24 supplies the flow of breathing gas from the flow generator 20 to an optional humidifier 32. The humidifier 32 provides humidity or vaporized liquid, such as water, to the flow of breathing gas received from the flow generator 20. The humidifier 32 outputs a flow of humidified breathing gas to the patient interface 14 through a suitable conduit, such as a second gases supply conduit 36. The humidifier 32 can output a flow of humidified breathing gas at a desired temperature and absolute humidity, such as an optimal temperature of about 37 degrees Celsius and absolute humidity of about 44 mg/L, or within a desirable or acceptable range of the optimal temperature and absolute humidity. The second gases supply conduit 36 can be a heated supply tube such that a temperature of the flow of breathing gas is maintained at an elevated level within the second gases supply conduit 36 and to avoid or limit condensation within the second gases supply conduit 36 or patient interface 14.

From the humidifier system 32, the flow of breathing gas is supplied to the patient interface 14, which can be any suitable type of interface capable of supplying a breathing gas to the respiratory system of the patient. The illustrated interface 14 is a nasal cannula having nasal prongs that are inserted into the nostrils of the infant patient 12. However, other suitable patient interfaces 14 can also be used, such as a face mask that covers the nose, or a mask that covers both the nose and mouth of the infant patient 12.

In some configurations, the system 10 is a biased flow system in which breathing gas is constantly flowing within the system 10 generally in a direction from the inlet of the patient interface 14 to the outlet of the patient interface 14. Thus, the infant patient 12 can inhale a portion of the flow of breathing gas and the remainder is passed through the patient interface 14. Exhaled or expiratory gases can mix with the flow of breathing gas and exit the patient interface 14 along with the unused portion of the flow of breathing gas. For convenience, the gases exiting the patient interface 14 are referred to as expiratory gases or the flow of breathing gas, although it is understood that either or both of patient exhaled gases and unused breathing gases can be present at any particular point in time.

Expiratory gases flow from the patient interface 14 to an expiratory pressure device 60, which is configured to regulate the minimum pressure within the system 10 to a level above ambient or atmospheric pressure. The expiratory pressure device 60 is connected to the patient interface 14 by a suitable conduit, such as an expiratory conduit 62. However, in an alternative arrangement, the expiratory pressure device 60 can be connected directly to or integrated with the patient interface 14.

The expiratory pressure device 60 is configured to provide a minimum pressure or minimum backpressure within the system 10 and, in particular, at the patient interface 14, which can be referred to as the positive end expiration pressure (PEEP). In the illustrated system 10, the expiratory pressure device 60 is an oscillatory valve capable of providing pressure oscillations relative to a mean PEEP pressure. It is believed that such pressure oscillations are beneficial to the infant patient 12 and may result in improved gas exchange and reduce the infant patient's 12 work of breathing. Thus, an oscillatory pressure expiratory pressure device 60 is particularly preferred. One type of oscillating pressure expiratory pressure device 60 is a fluid resistance valve, in particular a liquid or water resistance valve, which is often referred to as a bubbler. In general, a water resistance valve delivers the expiratory gases to an outlet that is submerged in a water reservoir resulting in a resistance to the exit of the expiratory gases that is greater than that caused by ambient or atmospheric pressure and related to the depth of the outlet relative to a surface of the water within the water reservoir. In some arrangements, the depth of the outlet is adjustable to allow the PEEP to be adjusted to a desired level. One suitable bubbler is the Bubble CPAP generator sold by the Applicant and Assignee of the present application. Preferably, the bubbler (or other oscillatory pressure device) is capable of producing vibrations in the infant patient's chest at a frequency of between about 5-30 Hz.

Figures 2, 3, 4:
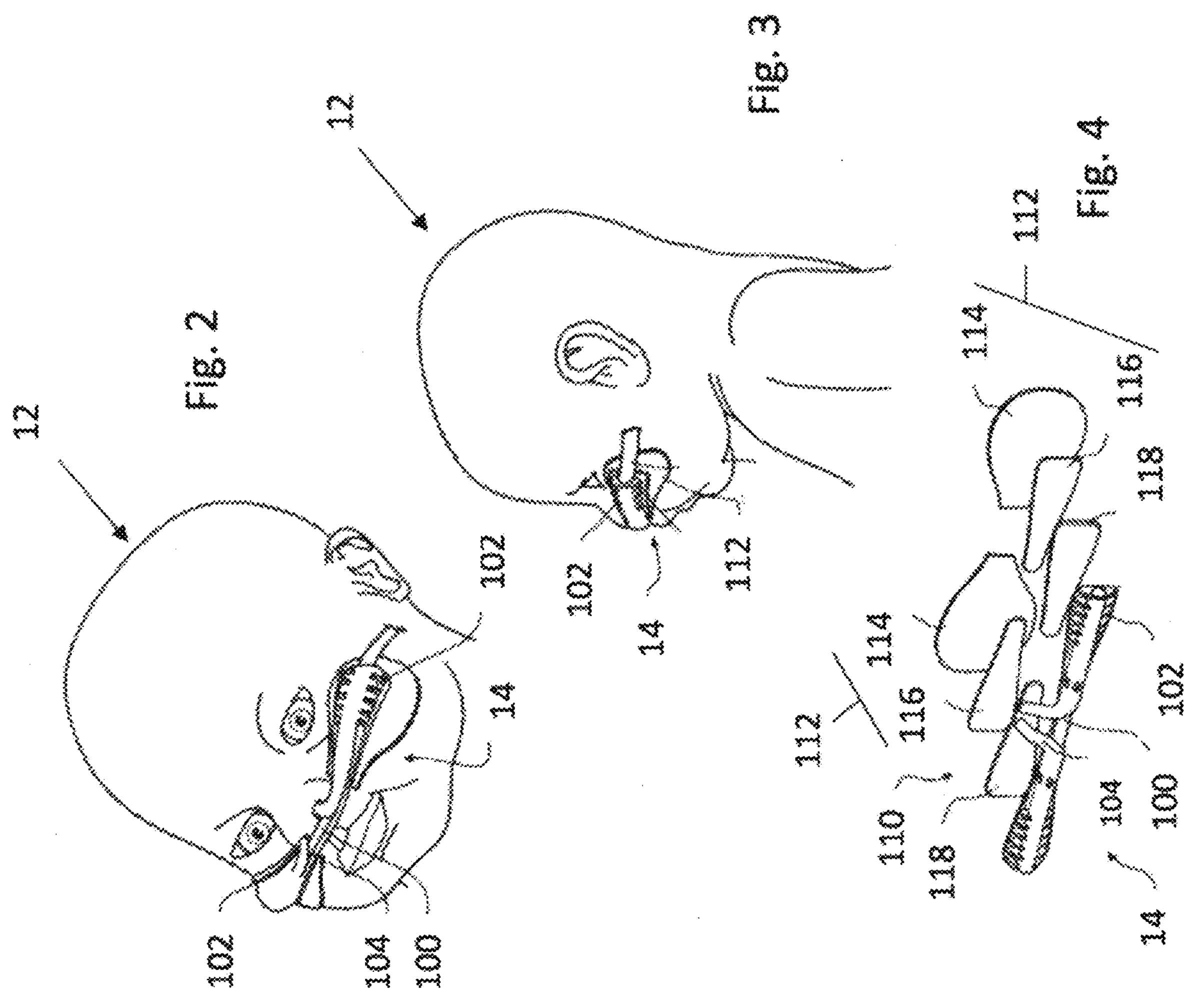
FIG. 2 illustrates an example patient interface in the form of a nasal cannula positioned in an operative position on the face of a user.
FIG. 3 is a side view of the user and nasal cannula of FIG. 2.
FIG. 4 is a perspective view of the nasal cannula of FIG. 2 with its constituent components separated from one another.

An example patient interface 14 in the form of a nasal cannula is illustrated in FIGS. 2-4. The patient interface 14 can include a central body portion 100 and a pair of side arms 102 extending in opposite lateral directions from the central body portion 100. In the illustrated arrangement, the central body portion 100 comprises one or more (e.g., a pair of) nasal elements 104, such as nasal prongs or nasal pillows. The patient interface 14 can be a sealing interface that contacts and creates a seal with a face of the patient 12. Accordingly, the nasal elements 104 of the nasal cannula can be configured to create a seal with the nares of the patient 12. Although a nasal cannula is shown, the patient interface 14 could also be in the form of a mask. In other words, the central body portion 100 could include a seal housing (e.g., a housing portion and a seal portion) configured to create a sealed chamber around a portion of the patient's 12 nose including the nostrils, the patient's 12 mouth, or both.

FIGS. 2-4 illustrate one arrangement for securing the patient interface 14 to the face of the patient 12. In the illustrated arrangement, the patient interface 14 is secured to the face (e.g., the cheeks or cheek regions) of the patient 12 at or along one or both side arms 102. The illustrated securement system 110 comprises a two-part releasable connection, which includes a pair of patches 112, 118 that are affixed to the patient 12 and the patient interface 14, respectively. In the illustrated arrangement, the securement system 110 is provided on each of the side arms 102 of the patient interface 14.

The first patch 112 comprises a dermal patch portion or dermal patch 114 that is adhered or otherwise attached to the patient's skin. The dermal patch 114 has a patient side that faces the patient's 12 skin and an interface side that faces the patient interface 14. The patient side of the dermal patch 114 may be attached to the skin of a patient by a dermatologically sensitive adhesive, such as a hydrocolloid. The patient interface side of the dermal patch 114 can be provided with the first part 116 of the two-part releasable connection of the securement system 110. The dermal patch 114 and the first part 116 of the securement system 110 can be integrated into a single component (the first patch 112) during the manufacturing process.

The second patch 118 is a patient interface patch. The second patch 118 also has a patient side and an interface side. The patient side of the second patch 118 is disposed adjacent the first patch 112 when the securement system 110 is engaged. The second patch 118 is or comprises the complimentary second part of the two-part releasable connection of the securement system 110 so that the respective parts of the two-part releasable connection are easily engaged with one another when the patches 112, 118 are brought together. The interface side of the second patch 118 is affixed to the patient interface 14. The second patch may be integrated with or suitably adhered to the patient interface 14, such as one or both side arms 102.

The two-part releasable connection may comprise a hook and loop fastener, a magnet or an array of magnets disposed on the respective patches with the poles suitably arranged, an adhesive arrangement that is activated when the patches are urged together, a post and aperture connection, an interlocking buckle or clip, or another suitable releasable coupling. In the illustrated arrangement, the two-part releasable connection comprises a hook and loop fastener. The first patch 112 may include one of a hook or a loop material and the second patch 118 may include the other of the hook or loop material, such that the patches 112, 118 are releasably attachable or connectable to each other.

Under some circumstances, it may be infeasible or undesirable to secure the patient interface 14 using the securement system 110 or another type of securement system that utilizes adhesion of one or more components to the patient' skin. For example, some patients may be too small for the first patch 112 to be properly accommodated on the cheeks or cheek regions. Or, the first patch 112 may not adhere to the patient's face for the full duration of the therapy. Under these circumstances, a headgear, such as the headgear 200 illustrated in FIGS. 5-10 or the headgear 300 illustrated in FIGS. 11-16, may be used as an alternative or supplemental support for the patient interface 14. The headgear 200, 300 could also be used with other patient interfaces, or could be modified for use with other interfaces.

Figure 5:
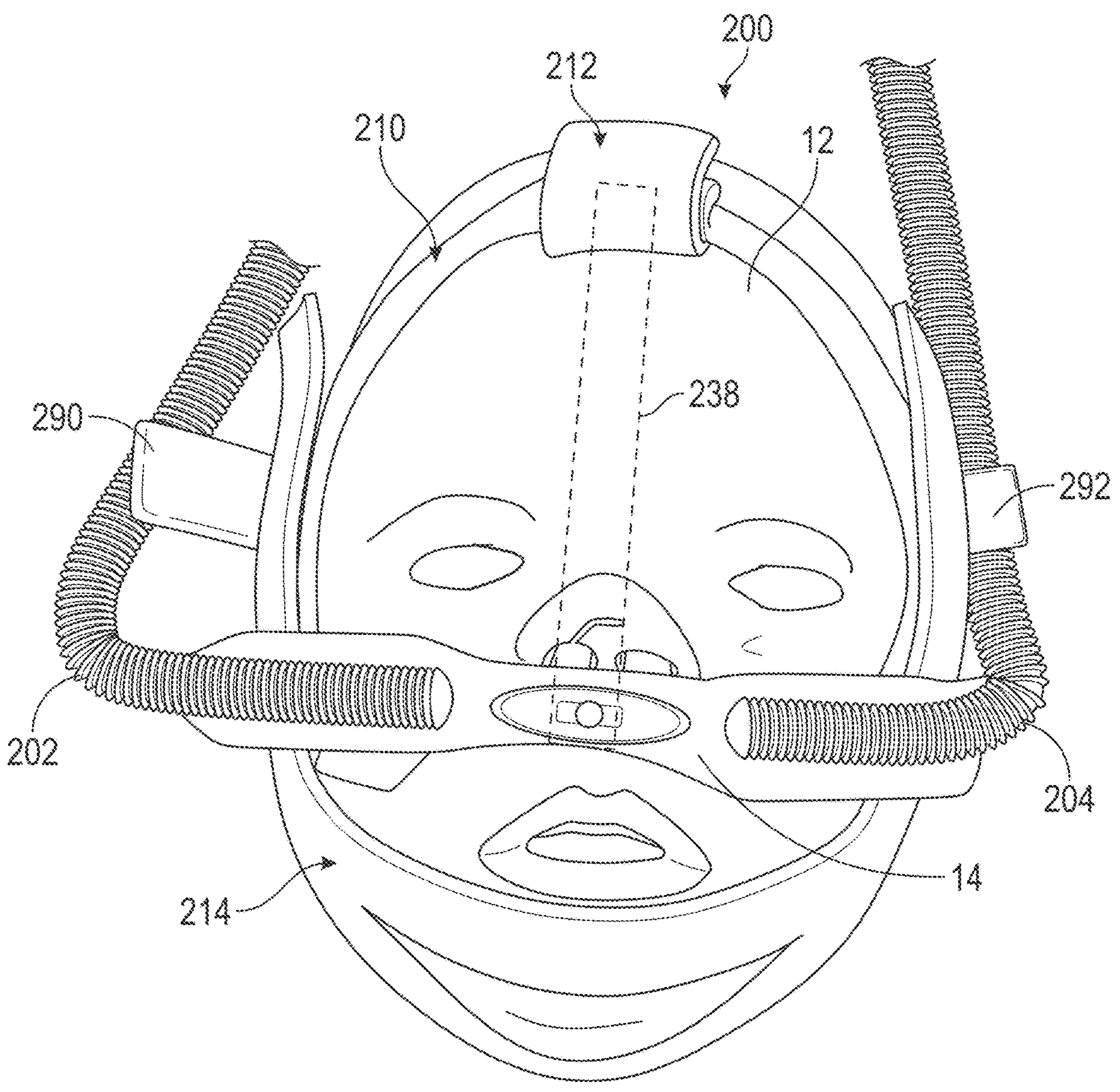
FIG. 5 is a front view of a headgear arrangement supporting a patient interface in the form of a nasal cannula on the face of a user.

As illustrated in FIG. 5, the patient interface 14 and the headgear 200 together form at least a portion of a patient interface assembly. The patient interface 14 includes an inspiratory conduit 202 configured to deliver the breathing gases to the nasal elements 104 of the patient interface 14. The inspiratory conduit 202 can be a portion of, or can be connected to, the second gases supply conduit 36 (FIG. 1). In the illustrated arrangement, the patient interface 14 includes an expiratory conduit 204 configured to convey expired gases and an unused portion of the breathing gases away from the central body portion 100 of the patient interface 14. The expiratory conduit 204 can be a portion of, or can be connected to, the expiratory conduit 62. As described above, in some configurations, the expiratory conduit 62 is connected to a resistance device, which can be the water resistance valve 60.

The patient interface 14 is supported in whole or in part by the headgear 200. In the illustrated arrangement, the headgear 200 includes a front portion 210, a rear portion 212, and a chinstrap 214. The patient interface 14 can be supported by and/or directly coupled to any portion or portions of the headgear 200, including without limitation any one or more of the front portion 210, the rear portion 212 and the chinstrap 214. The front portion 210, the rear portion 212 and the chinstrap 214 cooperate to form a support structure that is stable on the patient's 12 head so that the patient interface 14 can be held in a stable position by the headgear 200. In the headgear 200 of FIGS. 5-10, the front portion 210 and the rear portion 212 are separate structures that are coupled to one another in use. However, in other arrangements, at least portions of the front portion and the rear portion can be formed as a single structure. For example, as described further below, the headgear 300 of FIGS. 11-16 comprises a pair of side members that are coupled to one another in use, with each side member having a front portion and a rear portion.

Figure 6:
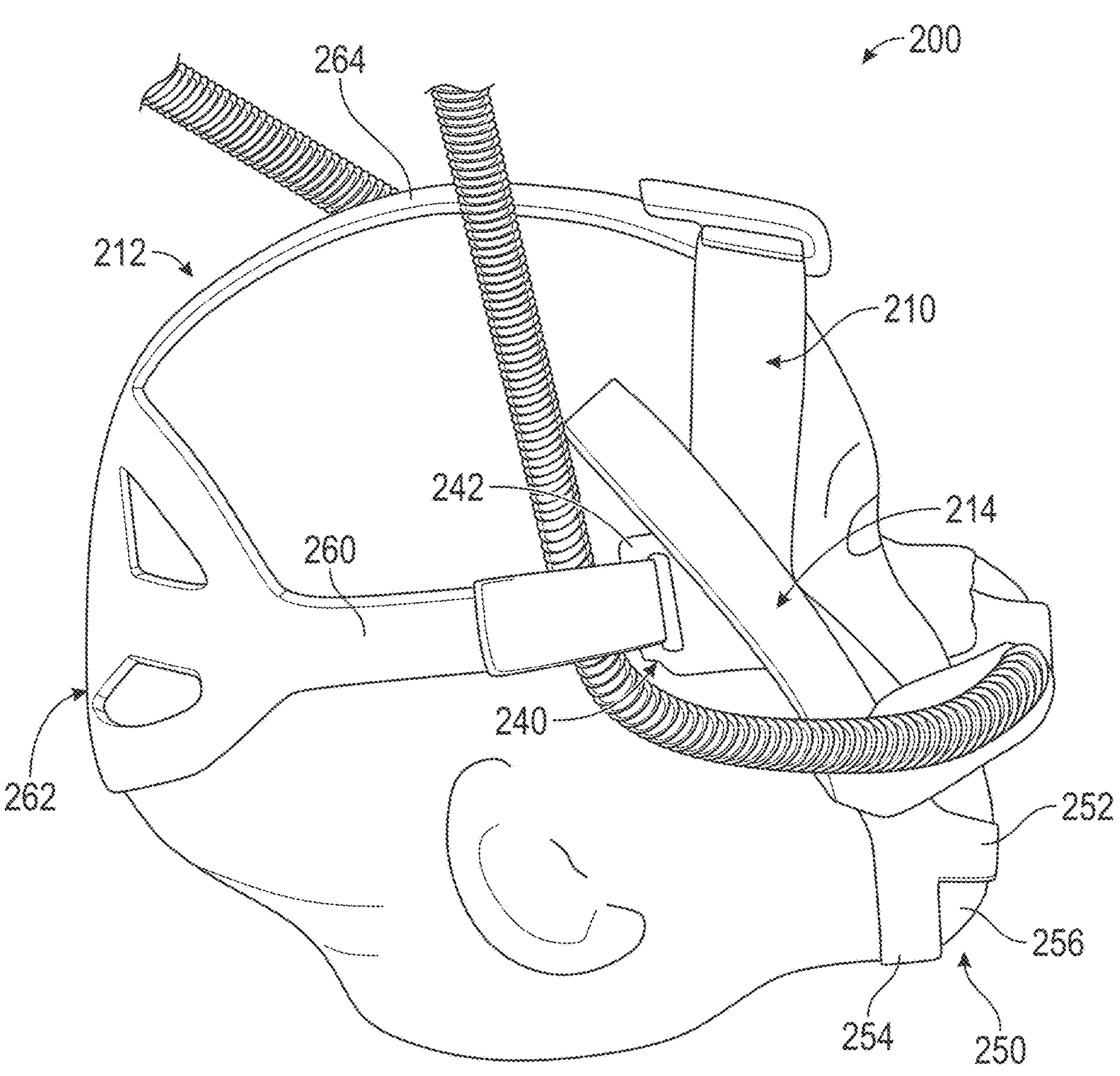
FIG. 6 is a side view of the headgear arrangement, nasal cannula and user of FIG. 5.
Figure 7:
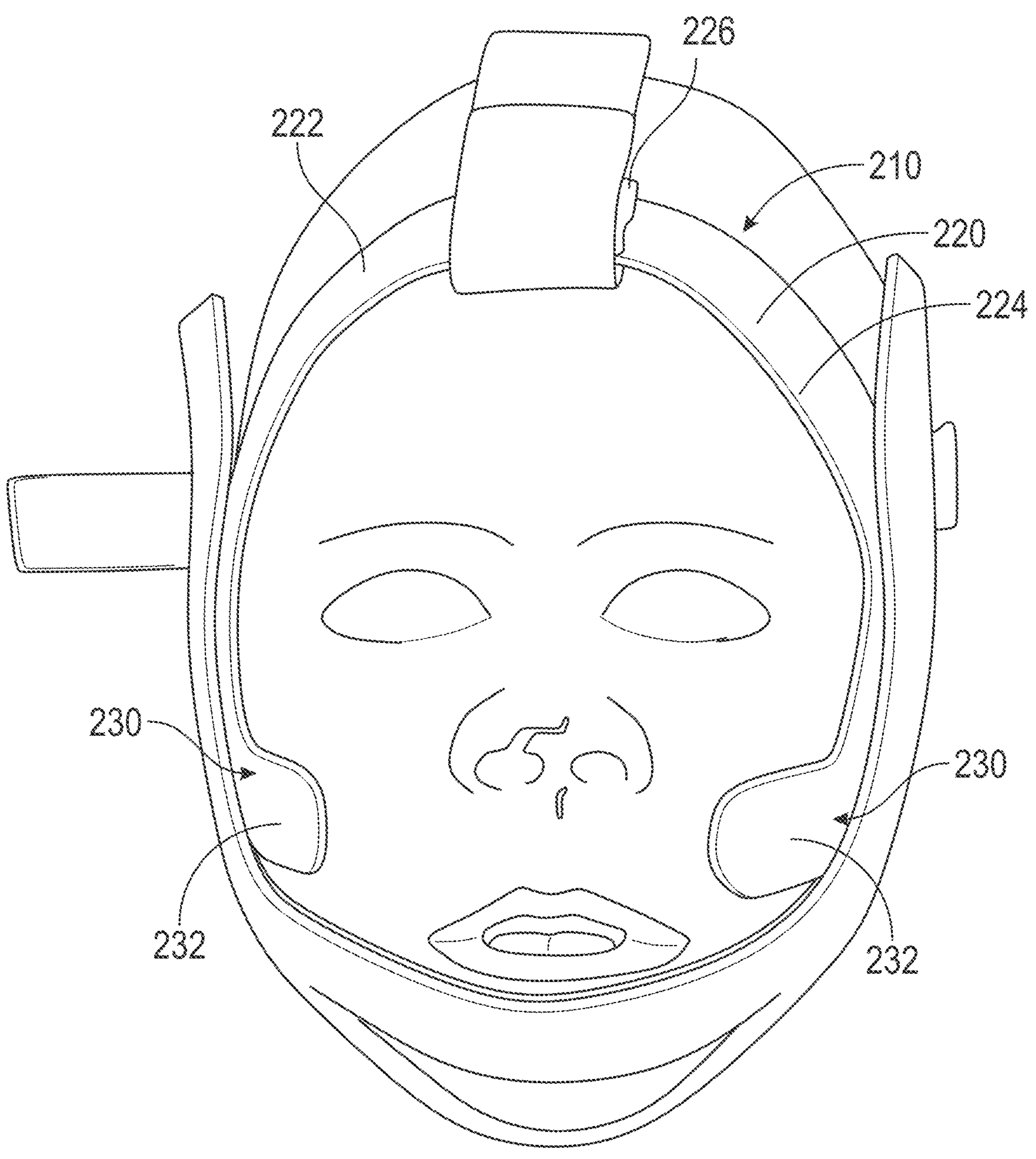
FIG. 7 is a front view of the headgear arrangement in place on the user with the nasal cannula omitted.
Figure 8:
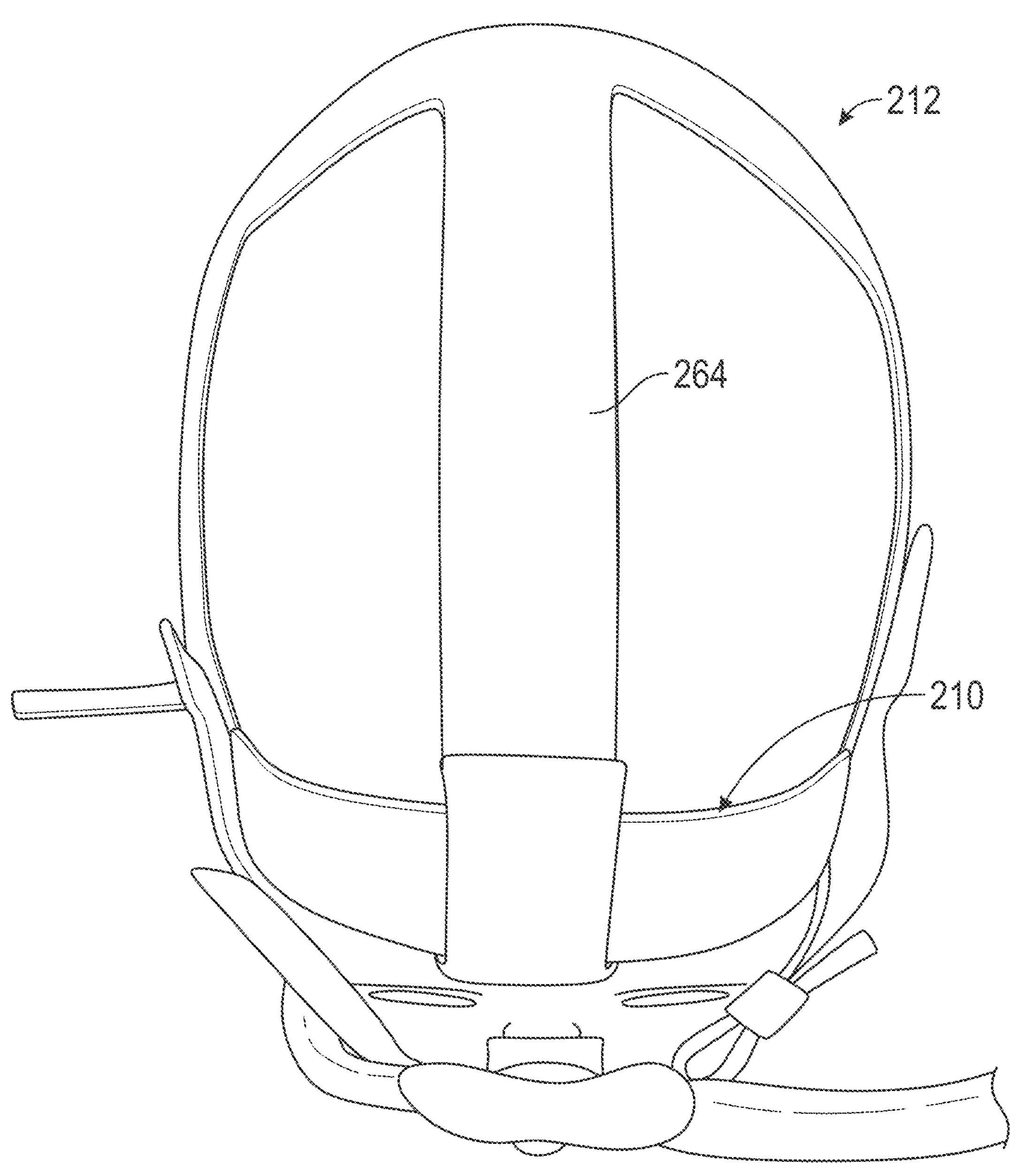
FIG. 8 is a top view of the headgear arrangement in place on the user.
Figure 9:
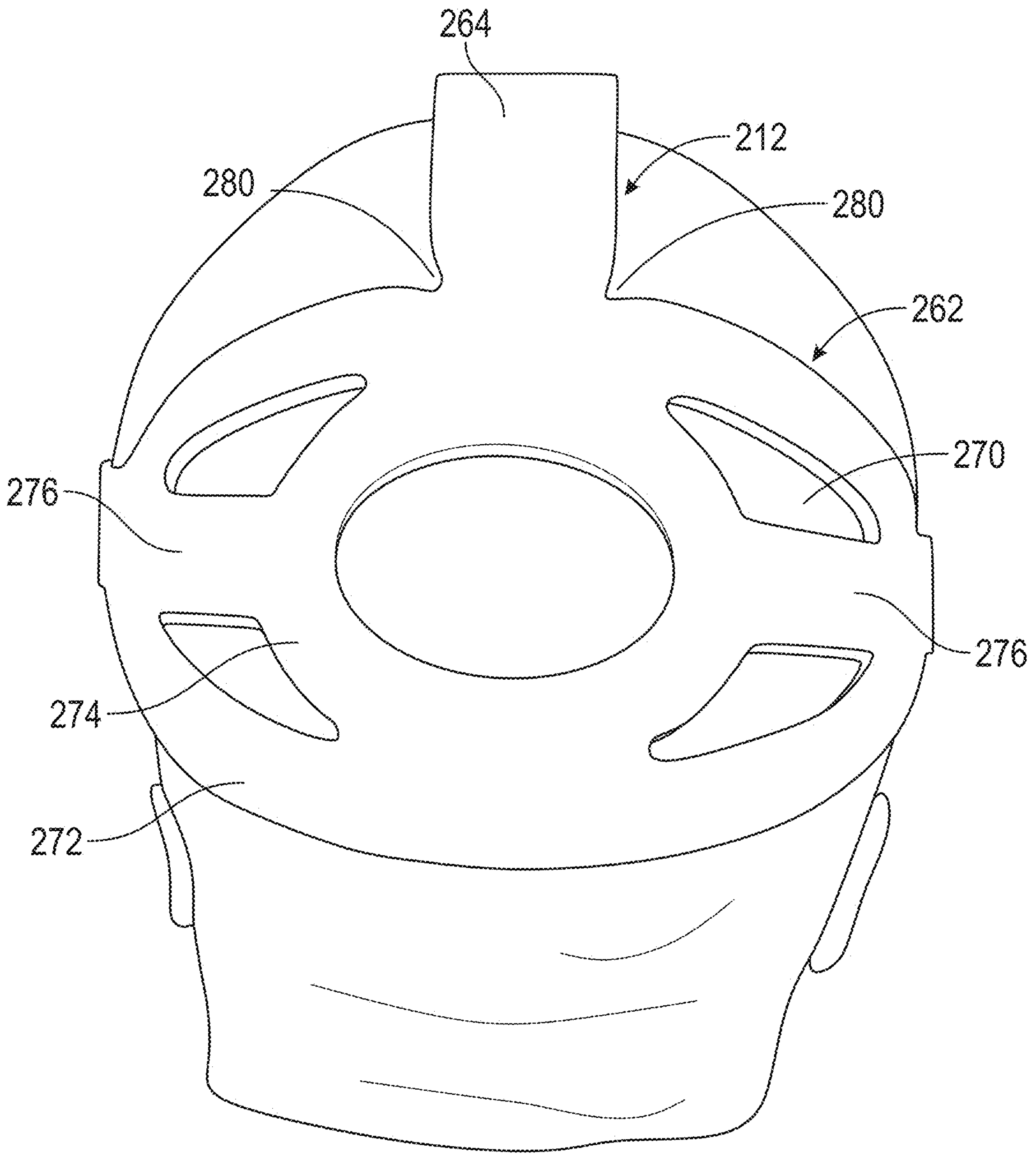
FIG. 9 is a rear view of the headgear arrangement in place on the user.

With particular reference to FIGS. 6 and 7, the front portion 210 comprises a strap 220 that is configured in use to extend over the patient's 12 head from one side to the other. In some configurations, the ends of the strap 220 are configured to be located at a level above the ears, such as at or near the temples of the patient 12. In some configurations, the strap 220 is configured to be located forward of a crown of the patient's 12 head. For example, the strap 220 can be configured to be located over a region corresponding to the rearward portion of the frontal bone or over a region corresponding to the junction between the frontal bone and the parietal bone of the patient 12.

The strap 220 can be adjustable in length. For example, the front portion 210 can include two portions 222, 224 that are connectable along a variable-length overlapping portion 226. By adjusting a length of the overlapping portion 226, an overall length of the front portion 210, or of a strap 220 of the front portion 210, can be adjusted to suit an individual patient 12. The overlapping portion 226 can be configured such that one strap portion 222 lies over top of and is releasably connectable to the other strap portion 224. For example, one strap portion 222, 224 can include a first part of a two-part connection and the other strap portion 222, 224 can include a second part of the two-part connection. The two-part connection can be the same as or similar to the two-part connection described above with respect to the securement system 110 or can be of another suitable arrangement.

Figure 10:
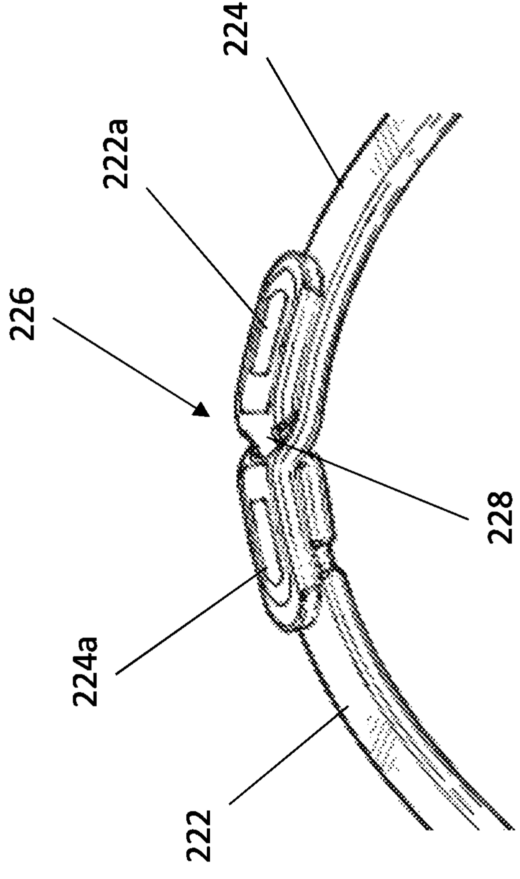
FIG. 10 is a perspective view of an example adjustment arrangement of a top strap of the headgear arrangement.

In one possible configuration, as shown in FIG. 10, one of the strap portions 222, 224 can include an opening 228 within the strap portion 222, 224 and the other of the strap portions 222, 224 can pass through the opening to create the overlapping portion 226. In such an arrangement, an end **222*a*, 224*a* of each strap portion 222, 224 is located on top of the other strap portion 222, 224. The end 222*a*, 224*a* of each strap portion 222, 224 can be releasably connectable to the other strap portion 222, 224. For example, the end 222*a*,224*a* of each strap portion 222, 224 can include a first part of a two-part connection and a portion of each strap portion 222, 224 spaced inwardly from a respective one of the ends 222*a*, 224*a* can include a second part of the two-part connection. The two-part connection can be the same as or similar to the two-part connection described above with respect to the securement system 110 or can be of another suitable arrangement. Alternatively, the strap 220 can be adjustable in a manner that does not create an overlap between the strap portions 222, 224. For example, each of the strap portions 222, 224 can pass through a buckle and be folded over onto, and attached to, themselves, as shown and described further below with reference to the headgear 300 of FIGS. 11-16**.

In some configurations, the front portion 210, or at least the strap 220 of the front portion 210, is flexible in torsion. That is, the front portion 210, or at least the strap 220, is flexible in a rotation direction around a longitudinal axis or a lengthwise direction of the front portion 210 or the strap 220. Such an arrangement can permit the front portion 210 to adapt to different head shapes. In some configurations, the front portion 210, or at least the strap 220, is non-stretchable, or substantially non-stretchable, at least in response to normal or expected forces during use. In some configurations, the front portion 210 comprises a plastic material to provide some or all of the non-stretch characteristics. The plastic material (or other material(s) of the front portion 210) can be combined with other materials, such as by a co-molding or an over-molding process, for example. In some configurations, the front portion 210 comprises a composite structure of a plastic core and a textile cover, wherein the cover and the core are attached by a permanent bond created by introduction of a molten material onto or into the cover, which is allowed to cool to form the core. Such an arrangement provides the benefits of plastic, with the soft appearance and touch of a textile strap. In some configurations, the front portion 210 comprises a thermoplastic elastomer (TPE) material. Other suitable materials may include any soft, flexible material, such as but not limited to a thermoplastic polyurethane (TPU), silicone or a non-stretch (or substantially non-stretch) fabric.

As described above, the patient interface 14 can be supported by and/or directly coupled to any portion or portions of the headgear 200, including without limitation any one or more of the front portion 210, the rear portion 212 and the chinstrap 214. In the illustrated arrangement, the patient interface 14 is supported at least by the front portion 210. The front portion 210 includes at least one attachment region. The illustrated front portion 210 includes an attachment region 230 on each side of the front portion 210. The illustrated attachment regions 230 are located at or near the respective ends of the strap 220, but could be located at any location along the strap 220, other region of the front portion 210 and/or other portion of the headgear 200. The attachment regions 230 are configured to support the patient interface 14 in a manner to maintain the patient interface 14 in a proper location on the patient 12, which may involve maintaining an adequate seal between the patient interface 14 and the patient 12 in use at least under normal circumstances. Accordingly, it can be desirable for the headgear 200 to maintain the attachment regions 230 in a stable position on the face of the patient 12 to provide a stable attachment location for the patient interface 14.

In the illustrated arrangement, the attachment region 230 is or comprises an attachment tab 232. The attachment tabs 232 are configured to support the patient interface 14. Each of the pair of attachment tabs 232 extends in a forward direction and is configured to lie generally across the cheek region of the patient 12, as illustrated in FIG. 7. The attachment tabs 232 are configured to be located generally in the same or a similar location as at least a portion of the first patch 112, as shown in FIGS. 2 and 3. The attachment tabs 232 may each be provided with a portion of a two-part connection that is complementary to the patch 118 of the patient interface 14, as shown in FIGS. 2-4. The portion of the two-part connection can cover a substantial entirety of the tab 232 and, in some configurations, may extend beyond the tab 232 onto a portion of the strap 220. That is, the attachment tabs 232 may function in a manner similar to the first patch 112. The portion of the two-part connection, which can for example be a hook portion of a hook and loop fastener, can be permanently attached to the attachment tab 232 of the front portion 210, such as by an over-molding operation. The shape and features of the attachment regions 230 and attachment tabs 232 can be the same as or similar to the attachment regions 230 and attachment tabs 232 of the headgear 300, as shown in and described with reference to FIG. 16.

Additional structures can also be provided that assist in maintaining the patient interface 14 in a suitable and/or stable location and/or orientation on the face of the patient 12. For example, the patient interface 14 can be provided with an optional third arm (in addition to the pair of side arms 102), which can be implemented as a forehead support 238 (FIG. 5). The optional forehead support 238 can be coupled to the patient interface 14 and can extend upwardly therefrom towards, to or beyond the forehead of the patient 14. An upper end of the optional forehead support 238 can be secured to the forehead of the patient 14, such as with a dermal patch as described herein, and/or can be secured to the headgear 200. For example, the optional forehead support 238 can be coupled (e.g., releasably coupled) to the front portion 210 and/or rear portion 212 of the headgear 200. The optional forehead support 238 can be coupled to the headgear 200 by any suitable arrangement, such as a two-part connection (e.g., hook and loop fastener), buckle, quick-release connector, or others.

In the illustrated arrangement, the front portion 210 includes a connection region 240 on each side at or near the respective ends of the strap 220 configured for connection with the rear portion 212. The illustrated connection region 240 comprises a buckle or loop 242 configured to receive a strap of the rear portion 212 to form at least a portion of a connection between the front portion 210 and the rear portion 212 of the headgear 200. In the illustrated arrangement, each of the connection regions 240 and/or loops 242 is located at or near a junction between the strap 220 and a respective one of the attachment regions 230 or tabs 232. The loop 242 extends from a rearward edge of the strap 220 in the illustrated arrangement to avoid overlap of the rear portion 212 and the front portion 210. However, the loop 242 could instead be located on or in front of the strap 220, if desired. Furthermore, other suitable types of connections can be used, such as two-part connections, interlocking buckles, post-and-aperture connections, or others.

The chinstrap 214 extends from one side to the other side of the headgear 200 and is configured to be positioned over the chin of the patient 12. Each end of the chinstrap 214 is configured to be connected to another portion of the headgear 200, such as one or both of the front portion 210 and the rear portion 212. In the illustrated arrangement, each end of the chinstrap 214 is connected to the front portion 210 of the headgear 200. The chinstrap 214 can be located on or near the ends of the strap 220. The chinstrap 214 can also overlie a portion of the attachment regions 230 or attachment tabs 232. The chinstrap 214 may be connected to the front portion 210 at the attachment region 230, such as by a two-part connection (e.g., hook and loop fastener). In addition, or in the alternative, the chinstrap 214 can be connected to the headgear 200 at one or both ends by a different type of connection, such as a loop or a quick-release buckle or clip to mitigate the risk of failure of the connection. In some configurations, the chinstrap 214 does not overlie the loops 242 and can be positioned forward of the loops 242 to facilitate adjustment of the rear portion 212. The chinstrap 214 can be configured to directly support the patient interface 14, either alone or in combination with the front portion 210, rear portion 212 and/or another portion of the headgear 200.

In some configurations, the chinstrap 214 is detachable from, or releasably connectable to, one or both of the front portion 210 and the rear portion 212. For example, each end of the chinstrap 214 can overlap or lie across one or both of the front portion 210 and the rear portion 212 and can be connected thereto with a suitable fastener. In some configurations, the ends of the chinstrap 214 can include a first part of a two-part connection and the front portion 210 and/or the rear portion 212 can include a second part of a two-part connection. The two-part connection can be the same as or similar to the two-part connection described above with respect to the securement system 110 or can be of another suitable arrangement. In some configurations, the front portion 210 and/or the rear portion 212 includes the hook portion of a hook and loop fastener so that the hook portion faces away from the patient's 12 face.

In some configurations, the chinstrap 214 is attachable to the front portion 210 and/or the rear portion 212 such that an effective length of the chinstrap 214 (e.g., a portion not overlapping with the front portion 210 and/or the rear portion 212) is adjustable. For example, the portion of the two-part connection can be located along a sufficient length of the chinstrap 214 such that the end portion of the chinstrap 214 can be connected to the front portion 210 and/or the rear portion 212 in a variety of different positions to adjust the effective length of the chinstrap 214.

In some configurations, the chinstrap 214 comprises a bifurcated portion 250 configured to be located at or along a chin of the patient 12. For example, the chinstrap 214 can include a first strap portion 252, or a forward strap portion, and a second strap portion 254, or a rearward strap portion. The first strap portion 252 and the second strap portion 254 cooperate to define an opening 256 therebetween. The opening 256 is configured to receive a portion of the patient's 12 chin, with the first strap portion 252 being located on a forward portion of the chin and the second strap portion 254 being located on a rearward portion of the chin. Such an arrangement facilitates proper location and retention of the chinstrap 214 on the patient 12.

The rear portion 212 of the headgear 200 is configured to engage a rear portion of the patient's 12 head and to retain the front portion 210 of the headgear 200 and the patient interface 14 in a proper position on the patient 12. The illustrated rear portion 212 includes a pair of side strap portions 260 located on an opposite sides of the headgear 200. The side strap portions 260 extend from a central section 262 of the rear portion 212. The central section 262 is configured to be located on a rear portion of the patient's 12 head in general opposition to the patient interface 12. In some configurations, the central section 262 can overlie a region corresponding to a rear portion of the parietal bone and/or the occipital bone. Each side strap portion 260 is configured to connect to a respective one of the loops 242. As illustrated in FIG. 6, for example, each side strap portion 260 is configured to be located above a level of the ear of the patient 12.

In some configurations, an effective length of the rear portion 212 is adjustable. In some configurations, the first and second side strap portions 260 define a respective one of a first end and a second end of the rear portion 212. Each end or strap portion 260 passes through a respective one of the buckles or loops 242, folds back on and attaches to itself. For example, an end of each of the strap portions 260 includes a first part of a two-part connection and an intermediate portion of each of the strap portions 260 includes a second part of the two-part connection. The two-part connection can be the same as or similar to the two-part connection described above with respect to the securement system 110 or can be of another suitable arrangement. For example, the two-part connection can be a hook and loop fastener. In some configurations, the end of each of the strap portions 260 comprises the hook portion of the hook and loop fastener and the intermediate portion of each of the strap portions 260 comprises the loop portion of the hook and loop fastener. In some configurations, at least the strap portions 260 can be constructed with an outer layer that is the loop portion of a hook and loop fastener.

In some configurations, the rear portion 212 comprises an optional midline strap 264 configured to extend over the top of the head of patient 12 in a forward-rearward or anterior-posterior direction. In the illustrated arrangement, the optional midline strap 264 is integrally formed with another portion or a remainder of the rear portion 212. However, in other arrangements the optional midline strap 264 could be releasably connectable to the remainder of the rear portion 212 so that it can be removed if desired, or can be omitted altogether. In those configurations in which it is used, the midline strap 264 can limit or prevent the headgear 200 from slipping down on the patient's 12 head. In the illustrated arrangement, the midline strap 264 originates at the central section 262 of the rear portion 212 and connects (e.g., releasably connects) to the front portion 210.

In some configurations, a length of the midline strap 264 is adjustable. For example, a forward end of the midline strap 264 can loop around the front portion 210 and connect to the front portion 210 and/or to itself. In some configurations, the end of the midline strap 264 can comprise a first part of a two-part connection and the front portion 210 and/or an intermediate portion of the midline strap 264 can comprise a second part of the two-part connection. The two-part connection can be the same as or similar to the two-part connection described above with respect to the securement system 110 or can be of another suitable arrangement. For example, the two-part connection can be a hook and loop fastener. In some configurations, at least an outwardly facing surface comprises the hook portion of the hook and loop fastener and the midline strap 264 comprises the loop portion of the hook and loop fastener. In some configurations, midline strap 264 can be constructed with an outer layer that is the loop portion of a hook and loop fastener.

In some configurations, the central section 262 comprises or defines an increased width portion of the rear portion 212. The increased width of the central section 262 can increase comfort for the patient 12 by spreading the retention force over a larger area to reduce the pressure on the patient's 12 head. The central section 262 can include one or more openings or cutouts 270. The cutouts 270 can increase the flexibility of the central section 262 to conform to the patient's 12 particular head shape and/or increase comfort by reducing the area for heat build-up underneath the central section 262.

In the illustrated arrangement, the central section 262 includes a plurality of cutouts 270. The cutouts 270 are arranged in a pattern that provides symmetry to the central section 262 along one or more axes or directions (e.g., a lengthwise direction and/or a widthwise direction). In the illustrated arrangement, the pattern of cutouts 270 in combination with an outer shape of the central section 262 defines at least one ellipse, such as a first ellipse 272 and a second ellipse 274, within the central section 262. The first ellipse 272 is larger and surrounds the second ellipse 274. Connecting strap portions 276 extend between the first ellipse 272 and the second ellipse 274 in a lengthwise direction of the central section 262. Such an arrangement provides an advantageous balance between conformability and support.

In some configurations, the rear portion 212 of the headgear 200 further comprises a notch 280 on each side of a junction between the midline strap 264 and the central section 262. The notches 280 cooperate to define a reduced width end portion of the midline strap 264 wherein the midline strap 264 intersects the central section 262. Such an arrangement provides some amount of decoupling between the midline strap 264 and the central section 262 and facilitates the ability of the midline strap 264 to conform to the curvature of the top of the head of the patient 12 without affecting or being affected by deformation of the central section 262 as it conforms to the curvature of the rear of the head of the patient 12.

The headgear 200 can include one or more tube management features configured to restrain breathing tubes of the system 10, such as the inspiratory conduit 202 and/or the expiratory conduit 204. In some configurations, the headgear 200 includes or is configured to define a tube management feature embodied as a loop 290 that secures the inspiratory conduit 202 in place relative to the headgear 200. In the illustrated arrangement, the loop 290 is defined by an end portion of the side strap 260 that passes through the loop 242 and is attached to itself. The end portion can also pass over the inspiratory conduit 202 after passing through the loop 242 and before attaching to itself to create a loop 290 that surrounds the inspiratory conduit 202. In the illustrated configuration, the headgear 200 includes or is configured to define a tube management feature embodied as a loop 292 that secures the expiratory conduit 204 in place relative to the headgear 200. The loop 292 can be formed in a manner similar to the loop 290, but from the other side strap 260. In other configurations, the loops 290, 292 can be formed separately from the side straps 260, such as by dedicated strips of material. Other suitable retention mechanisms can also be used. For example, the conduits 202, 204 can include one part of a two-part connection and the headgear 200 (e.g., the rear portion 212) can include the other part of the two-part connection so that the conduit 202, 204 can be secured to the headgear 200. The two-part connection can be the same as or similar to the two-part connection described above with respect to the securement system 110 (e.g., a hook and loop fastener) or can be of another suitable arrangement.

In some configurations, different parts or portions of the headgear 200 have different stretch properties. For example, any one of the front portion 210, rear portion 212 and chinstrap 214 can have different stretch properties relative to any other of the front portion 210, rear portion 212 and chinstrap 214. As used herein, stretch refers to elongation (e.g., percent elongation) of the headgear 200 in response to an applied load. Such elongation may relate to the elasticity of the material or materials form which the headgear 200 or portion thereof is constructed. Stretch may occur in one or more directions. Often, the relevant stretch is in a direction generally along a length or an effective length of the headgear 200 or portion thereof. For example, the relevant stretch can be along a lengthwise direction of the strap 220 of the front portion 210, the side straps 260 or midline strap 264 of the rear portion 212, or the end portions of the chinstrap 214. However, the relevant stretch can refer to a direction generally along a width or an effective width of the headgear 200 or portion thereof, or both the length and width directions.

Stretch may not be uniform over an entire length (or width) of the portion (e.g., front portion 210, rear portion 212 or chinstrap 214). Thus, a comparison of the stretch of different components or portions can compare a change in overall length, or effective overall length, of the components or portions. For example, a degree of stretch of the front portion 210 can relate to the elongation (e.g., percent elongation) of the strap 220 in response to a given load. For example, a degree of stretch of the rear portion 212 can relate to the elongation (e.g., percent elongation) of the rear portion 212 between the end of one of the side straps 260 to the end of the other of the side straps 260 in response to a given load. For example, a degree of stretch of the chinstrap 214 can relate to the elongation (e.g., percent elongation) of the strap 220 in response to a given load. For the purpose of comparison between the different components or portions of the headgear 200, the load applied should be consistent between the components or portions.

In some configurations, the chinstrap 214 is a stretch component, which possesses some amount of stretch so that the chinstrap 214 can be tensioned when applied and/or can maintain tension in use. A tensioned chinstrap 214 can enhance the ability of the chinstrap 214 to maintain the headgear 200 properly positioned on the head of the patient 12. The degree of stretch of the chinstrap 214 may be selected to permit the patient 12 (e.g., an infant patient) to open his or her mouth while the chinstrap 214 is in use. The chinstrap 214 can be configured to encourage the patient 12 to normally keep his or her mouth closed, but can permit deliberate opening of the mouth. The degree of stretch of the chinstrap 214 maybe selected to permit stretching of the chinstrap 214 to accommodate other facial movements of the patient 12, including but not limited to those that occur during side sleeping, while allowing a portion or a remainder of the headgear 200 to maintain a relatively stable position on the head of the patient 12 to maintain a sufficient seal and/or position of the patient interface 14.

In some configurations, the chinstrap 214 has a greater degree of stretch than one or both of the front portion 210 and the rear portion 212. In some configurations, the chinstrap 214 has a degree of stretch, or a percentage elongation, that is significantly greater than the degree of stretch of the front portion 210 and/or the rear portion 212 and/or a remainder of the headgear 200. Such arrangements allow the chinstrap 214 to stretch if the patient 12 opens his or her mouth, while the remainder of the headgear 200 tends to stay in place. In other words, the greater degree of stretch of the chinstrap 214 allows the chinstrap 214 to preferentially stretch in response to the patient 12 opening his or her mouth, so that such movement is primarily or completely accommodated by the chinstrap 214. Under such circumstances, the stretch, if any, of the front portion 210 and/or the rear portion 212 can be less than or significantly less than the stretch of the chinstrap 214.

In some configurations, the degree of stretch of the front portion 210 is substantially non-stretch. In some configurations, the degree of stretch of the rear portion 212 is substantially non-stretch. As used herein, substantially non-stretch means that the component or portion does not stretch under normal or expected loads experienced during use, or does not stretch to an extent that negatively impacts the ability of the headgear 200 to maintain a proper or effective position of the patient interface 14 on the face of the patient 12.

FIGS. 11-16 illustrate another example headgear 300 configured to support the patient interface 14, which is embodied as a nasal mask. The patient interface 14 is supported in whole or in part by the headgear 300. The headgear 300 provides a support structure that is stable on the patient's 12 head so that the patient interface 14 can be held in astable position by the headgear 300. The headgear 300 can be similar in some respects to the headgear 200 of FIGS. 5-10, and is described in the context of differences relative to the headgear 200. Features of the headgear 300 not described in detail can be the same as or similar to corresponding features of the headgear 200, or can be of another suitable arrangement. In addition, features of each headgear 200, 300 can be implemented on the other headgear 200, 300. For example, the chin strap 214 of the headgear 300, or specific features thereof, can be used with the headgear 200 and vice-versa.

The illustrated headgear 300 of FIGS. 11-16 includes a pair of side members 302, 304 that are coupled to another to form a portion or an entirety of the headgear 300. In some configurations, the side members 302 are adjustably coupled to one another. The provision of two side members 302, 304 that are adjustably coupled allows for adjustment of a size (e.g., a perimeter length or circumference) of the headgear 300 in a manner similar to the separate front portion 210 and rear portion 212 of the headgear 200 of FIGS. 5-10. However, in other arrangements, the side members 302, 302 can be non-adjustable, permanently coupled and/or integrally formed.

In the illustrated arrangement, the side members 302, 304 of the headgear 300 each comprise a front portion 306 and a rear portion 308, which can correspond from a functional standpoint, with respect to one or more functions, with the front portion 210 and the rear portion 212, respectively, of the headgear 200. Thus, references herein to the front portion and the rear portion of a headgear can equally apply to portions formed separately or portions formed as a single piece, including but not limited to the specific example portions 210, 212, 306 and 308.

In the illustrated arrangement, the side members 302, 304 are coupled to one another to form a portion or an entirety of the headgear 300. The illustrated side members 302, 304 are coupled to one another substantially along a midline of the head of the patient 12. However, in other arrangements, the side members 302, 304 can be coupled to one another at different locations (e.g., offset from a midline of the head of the patient 12) or can include an additional member (e.g., a central member) intermediate the side members 302, 304.

Figure 16:
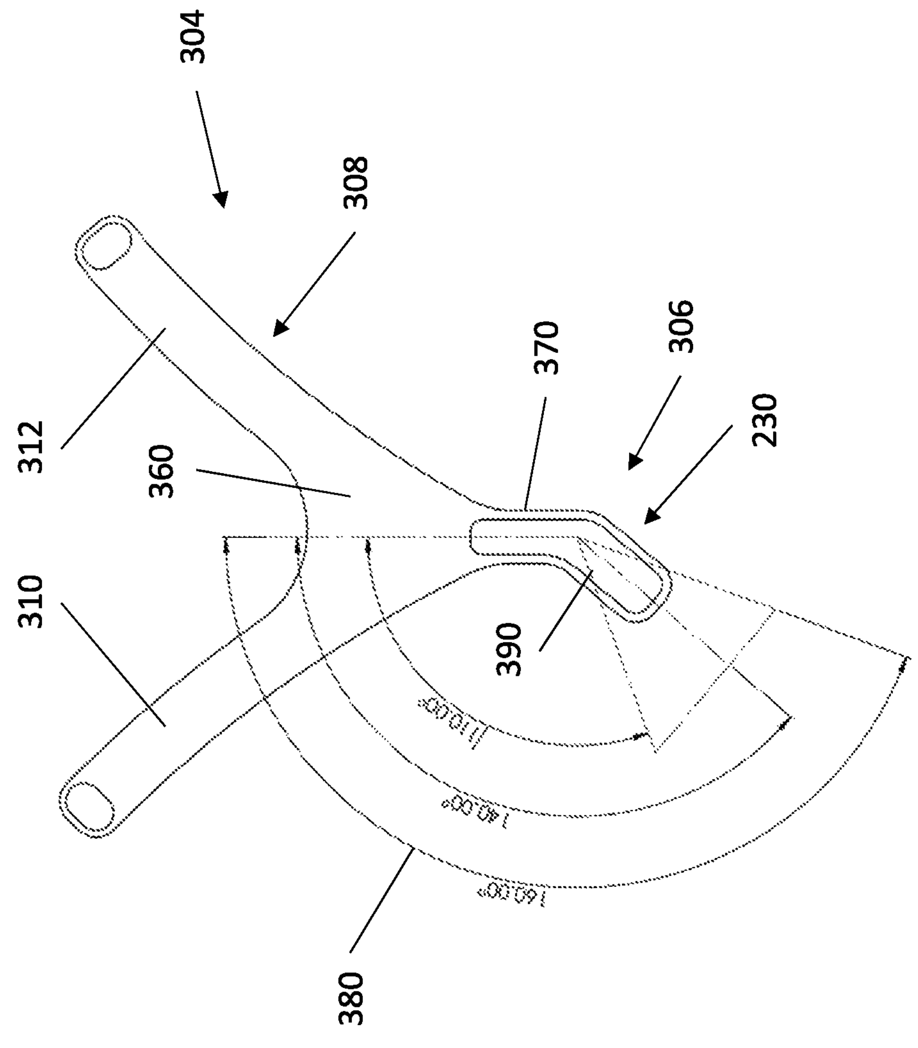
FIG. 16 is a side view of a side of the headgear arrangement of FIG. 11 shown separate from the user and in a planar or laid-flat orientation.

In the illustrated arrangement, the side members 302, 304 are mirror images of one another or are substantially mirror images from one another. In other words, the side members 302, 304 can be mirror images in basic shape; however, one of the side members 302, 304 can include additional structure or features not shared by the other of the side members 302, 304. For example, the side members 302, 304 can include different parts of a two-part connector. FIG. 16 illustrates the side member 304 configured to be positioned on the left side of the patient 12 in a planar or laid-flat orientation. In the illustrated arrangement, the side member 302 configured to be positioned on the right side of the patient 12 can be a mirror image of the side member 304. Accordingly, structures, features or other aspects of the side member 302 can be assumed to be the same as or similar to the corresponding structures, features or other aspects described with respect to the side member 304, except mirrored relative thereto.

The illustrated headgear 300 includes the side members 302, 304 releasably connected to one another. In some configurations, the side members 302, 304 can be adjustably coupled to one another such that a relative position of the side members 302, 304 can be varied to suit a variety of patients 12. Adjustment of the relative position of the side members 302, 304 can permit adjustment of a location of the attachment region 230 relative to the face of a particular patient 12 so that the patient interface 14 can be properly positioned. As described above, the location of the attachment region 230 can be generally overlying the cheek or cheek region of the patient 12, such as in the location illustrated and described with respect to FIGS. 2-4. Additional details of an example attachment region 230 are described further below with reference to FIG. 16.

In some configurations, each of the side members 302, 304 includes at least one strap. In some configurations, each of the side members 302, 304 includes multiple straps. In some configurations, each of the side members 302, 304 includes a top strap 310. In some configurations, each of the side members 302, 304 includes a rear strap 312. In the illustrated arrangement, each of the side members 302, 304 includes the top strap 310 and the rear strap 312. The top strap 310 and the rear strap 312 of one of the side members 302, 304 is connected to a respective one of the top strap 310 and the rear strap 312 of the other of the side members 302, 304 such that the top straps 310 cooperate to form a top strap 310 of the headgear 300 and the rear straps 312 cooperate to form a rear strap 312 of the headgear 300. In the illustrated arrangement, the top strap 310 is a crown strap or coronal strap, which is located further rearward on the head of the patient 12 than the strap 220 of the headgear 200. The top strap 310 can overlie a region corresponding to a top or forward portion of the parietal bone of the patient 12. The rear strap 312 can be positioned similarly to the central section 262 of the headgear 200. The rear strap 312 can overlie a region corresponding to the rear portion of the parietal bone and/or the occipital bone. However, other positioning of the straps 310, 312 can also be used, such as positions the same as, or similar to, those of the strap 220 and the central section 262 of the headgear 200.

The top strap 310 and the rear strap 312 of one of the side members 302, 304 is connected to a respective one of the top strap 310 and the rear strap 312 of the other of the side members 302, 304 by a buckle 314. The buckle 314 includes two openings through which a strap 310, 312 of a respective side member 302, 304 passes. The straps 310, 312 then fold over onto themselves and are secured to themselves with a suitable fastener, such as a two-part connection (e.g., a hook and loop fastener). However, other suitable connections between the straps 310, 312 of the side members 302, 304 can also be used. For example, the straps 310, 312 can be secured to (e.g., adjustably secured to) a respective portion of a quick-release clip or buckle and the portions of the clip or buckle can connect to or disconnect from one another.

In some configurations, the headgear 300 includes a chinstrap 320. The chinstrap 320 can be similar to the chinstrap 214 and can function to assist in maintaining the side members 302, 304 and/or other portion of the headgear 300 in a stable position on the head of the patient 12. For example, the chinstrap 320 can permit the patient 12 (e.g., an infant patient) to open his or her mouth or to accommodate other facial movements of the patient 12 while allowing a portion or a remainder of the headgear 300 to maintain a relatively stable position on the head of the patient 12 to maintain a sufficient seal and/or position of the patient interface 14. The chinstrap 320 can be configured to encourage the patient 12 to normally keep his or her mouth closed, but can permit deliberate opening of the mouth.

In the illustrated arrangement, one or both ends of the chinstrap 320 includes a grip portion or a grip tab 330. The grip tab 330 can be configured to facilitate gripping by a caregiver or the patient 12 to allow for ease of adjustment of the position of the end of the chinstrap 320 on the side member 302, 304 (or other portion of the headgear 300) and/or allow the chinstrap 320 to be tensioned to a desirable degree. In some configurations, the grip tab 330 can be a feature that is over-molded onto the underlying material of the chinstrap 320. However, in other configurations, the grip tab 330 can be formed separately from and attached to the chinstrap 320 by a suitable connection, such as mechanical fasteners or an adhesive connection.

The chinstrap 320 can include a chin retention feature 340, which can be an alternative to the bifurcated portion 250 of the chinstrap 214. In the illustrated arrangement, the chin retention feature 340 of the chinstrap 320 comprise a retention element 342, which can be a gripper and/or a chin receptacle or chin cup. In some configurations, the retention element 342 is in the form of a chin cup, which defines a concave surface that receives a portion of the chin of the patient 12. In some configurations, the retention element 342 is constructed from or comprises a material that has good grip characteristics (e.g., a high coefficient of friction) with human skin. In some configurations, the retention element 342 both receives a portion of the chin of the patient 12 and includes a material having good grip characteristics. In some configurations, the retention element 342 is over-molded onto the underlying material of the chinstrap 320. However, in other configurations, the retention element 342 can be formed separately from and attached to the chinstrap 320 by a suitable connection, such as mechanical fasteners or an adhesive connection. In some configurations, a suitable material is TPE, TPU, silicone or another similar material.

The retention element 342 can be wider than a width of the underlying strap portion of the chinstrap 320 and/or a portion of the chinstrap 320 immediately adjacent the retention element 342. In the illustrated configuration, the retention element 342 includes a central opening that exposes the underlying strap portion of the chinstrap 320. The surface facing the patient 12 can be fully covered by the retention element 342 or could similarly have an opening that exposes the underlying strap portion of the chinstrap 320. In some configurations, a retention element 342 could be provided to one or both of the first strap portion 252 and the second strap portion 254 of the bifurcated portion 250 of the chinstrap 214.

In some configurations, the headgear 300 can include one or more tube management features configured to restrain breathing tubes of the system 10, such as the inspiratory conduit 202 and/or the expiratory conduit 204. For example, the headgear 300 can include tube management features such as those described above with respect to the headgear 200. In the illustrated arrangement, the headgear 300 includes a tab 350 that can be secured to the headgear 300 at each end to define a loop, along with a portion of the headgear 300 (e.g., one of the side members 302, 304), through which the tube (e.g., 202 or 204) can pass. In some configurations, one end (e.g., a rearward end) of the tab 350 is permanently secured to the portion of the headgear 300 and the other end (e.g., a forward end) of the tab 350 makes are leasable connection with the portion of the headgear 300 by a suitable releasable fastener, such as a two-part connection (e.g., hook and loop fastener). In other arrangements, the tab 350 can be secured to the portion of the headgear 300 at an intermediate location and the ends of the tab 350 can be secured together to form a loop. Other suitable tube management arrangements can also be used, such as providing one part of a two-part connection on the tube (e.g., 202 or 204) and the other part of the two-part connection on the portion of the headgear 300. The two-part connection can be the same as or similar to the two-part connection described above with respect to the securement system 110 (e.g., a hook and loop fastener) or can be of another suitable arrangement.

Figure 11:
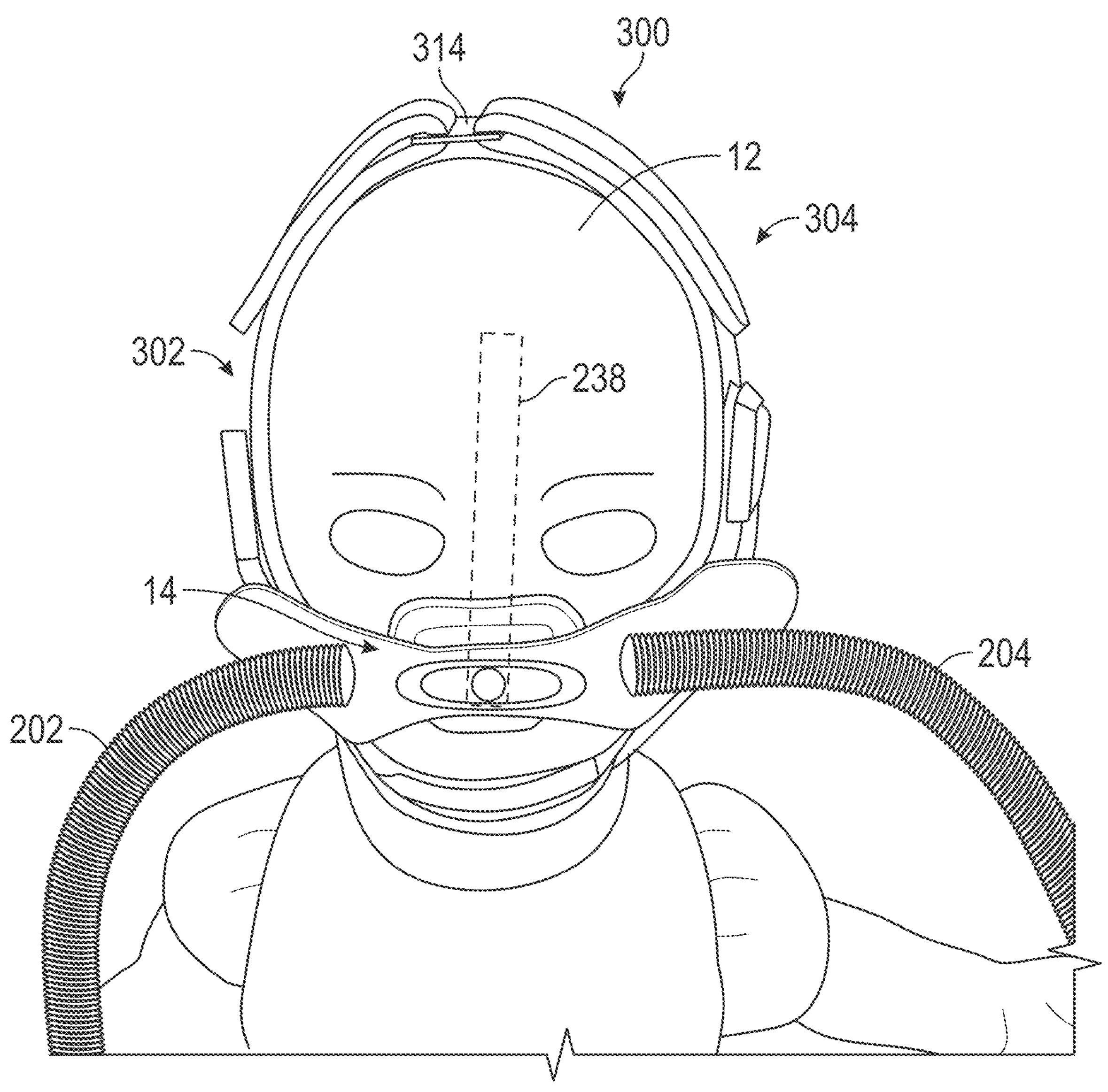
FIG. 11 is a front view of another example headgear arrangement supporting an example patient interface in the form of a nasal mask positioned in an operative position on the face of a user.
Figure 12:
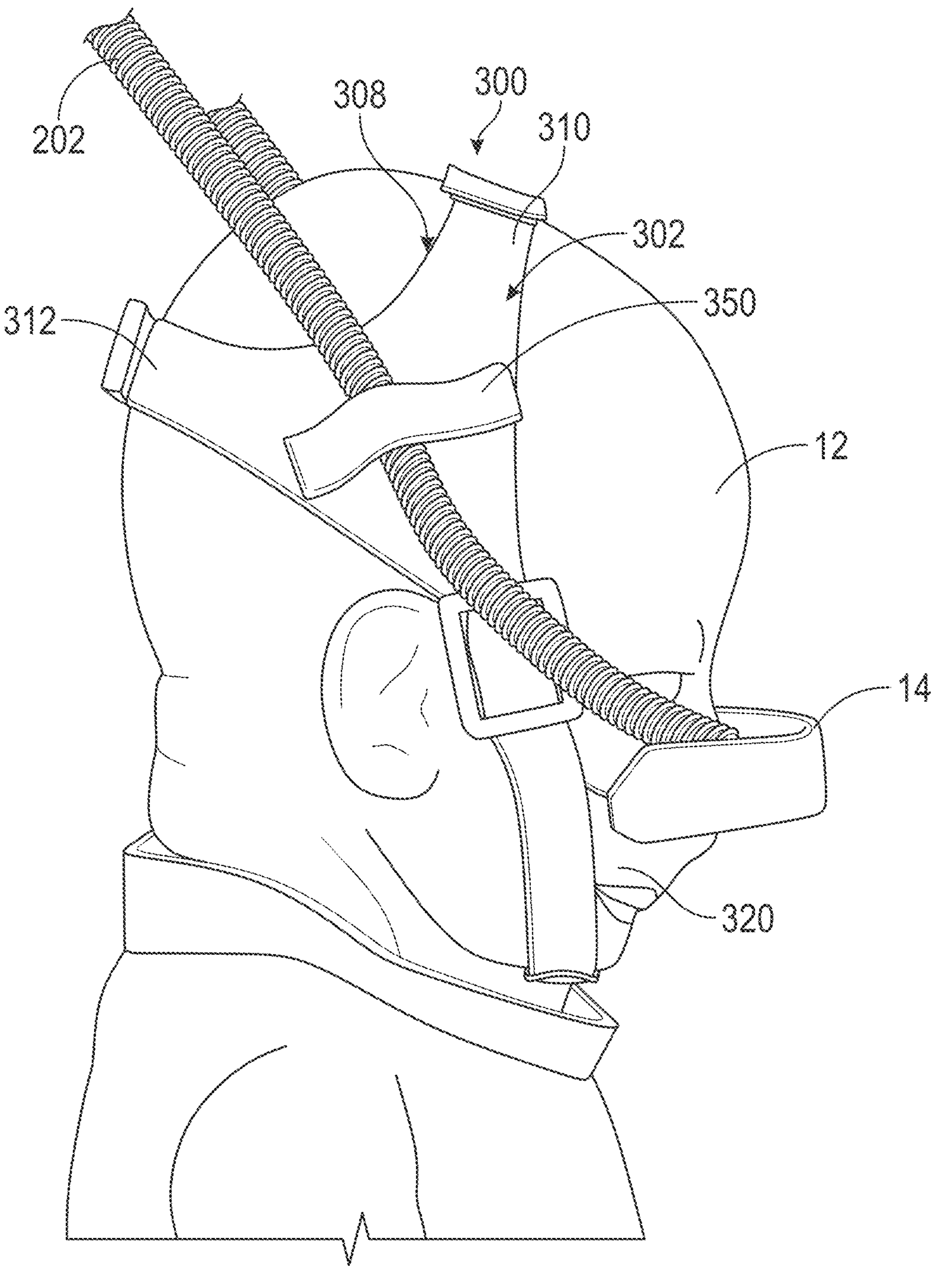
FIG. 12 is a side view of the headgear arrangement, nasal mask and user of FIG. 11.
Figure 13:
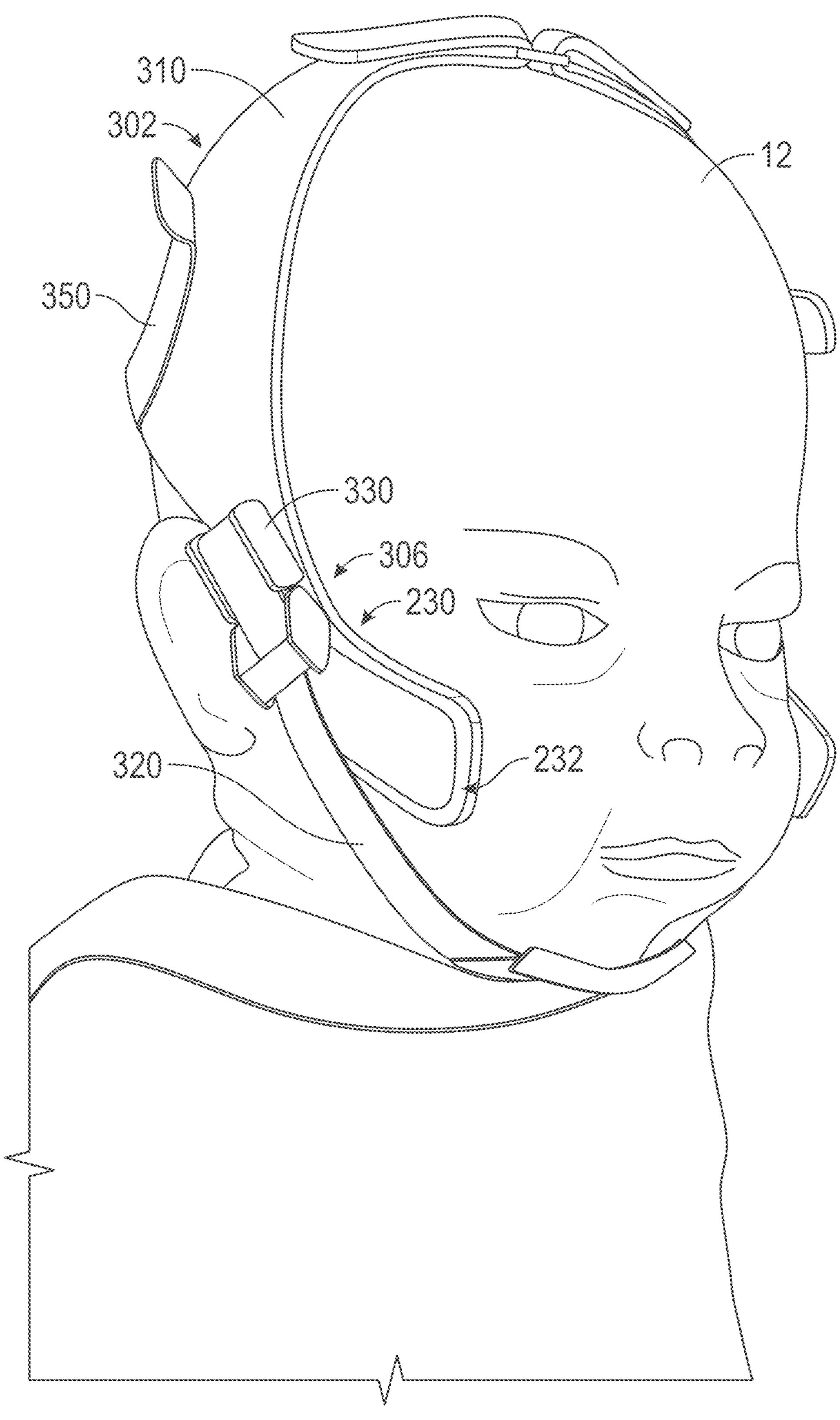
FIG. 13 is a perspective view of the headgear arrangement and user of FIG. 11 with the nasal mask omitted.
Figure 14:
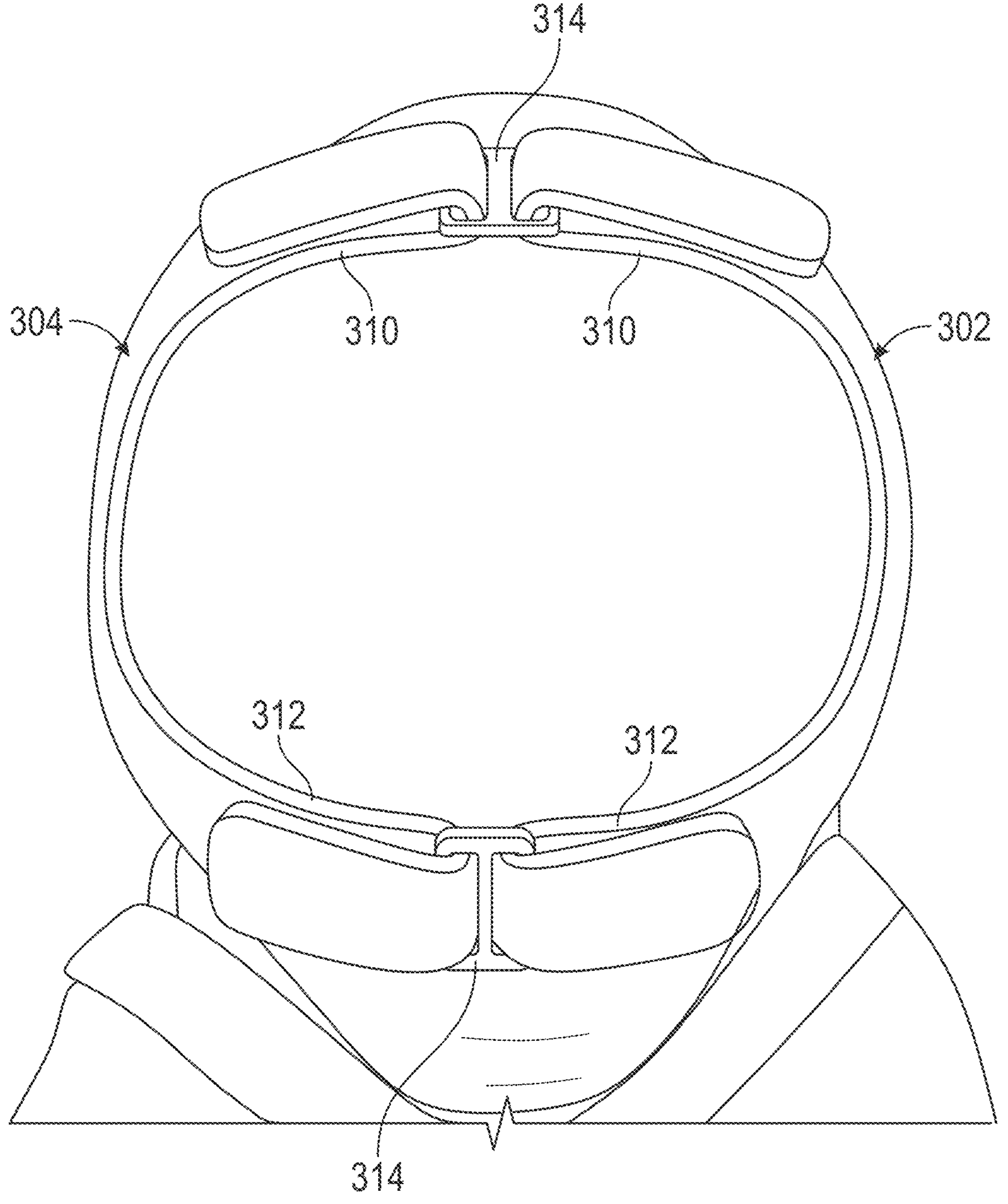
FIG. 14 is a top view of the headgear arrangement and user of FIG. 11 showing upper and rear adjustments of the headgear arrangement.
Figure 15:
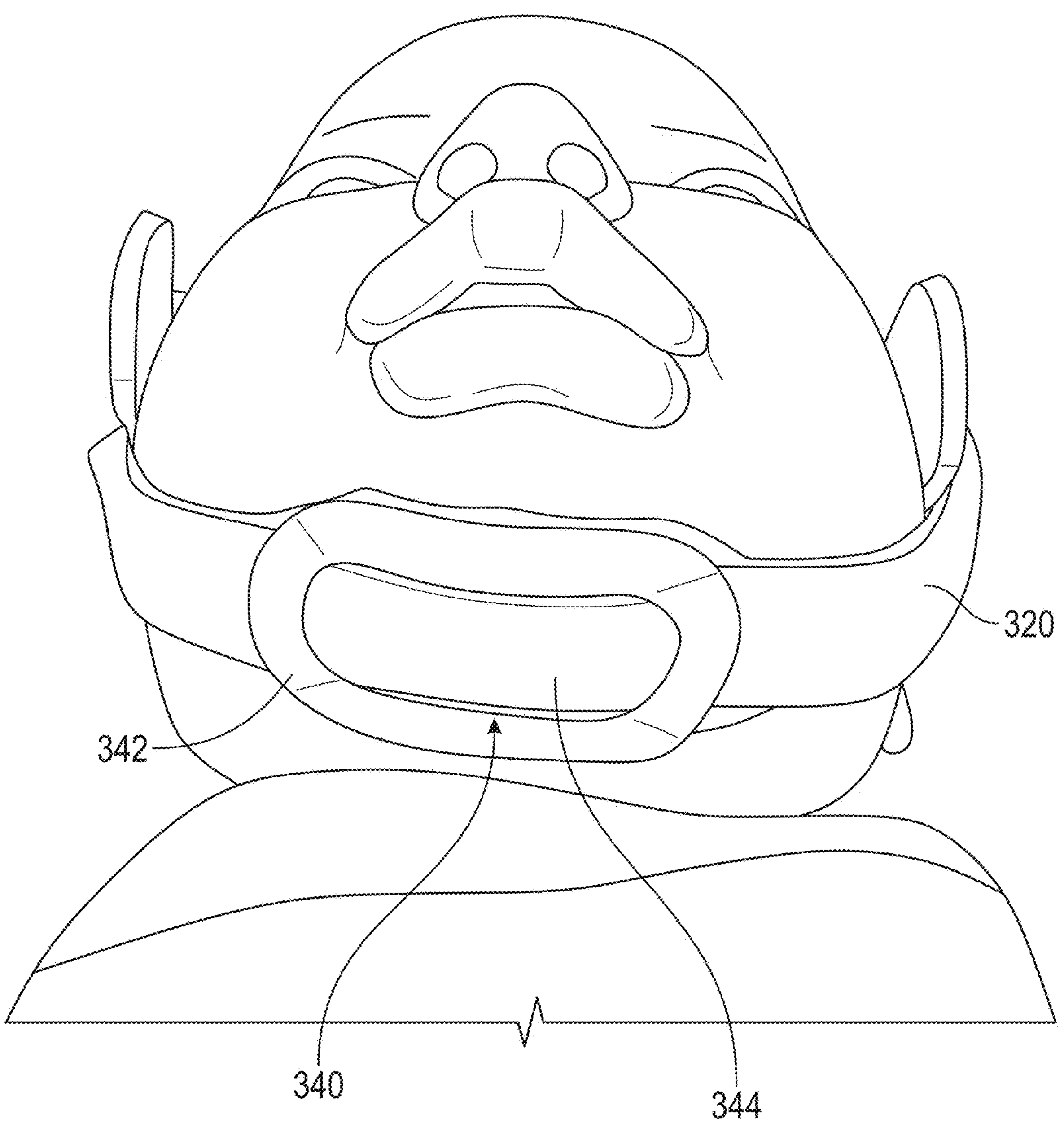
FIG. 15 is a bottom view of the headgear arrangement and user of FIG. 11 showing a chin strap engaged with the chin of the user.

With reference to FIG. 11, the patient interface 14 can optionally include a third arm (in addition to the pair of side arms 102), which can be implemented as a forehead support 238 in a manner to that described in connection with FIG. 5. The optional forehead support 238 can be coupled to the patient interface 14 and can extend upwardly therefrom towards, to or beyond the forehead of the patient 14. An upper end of the optional forehead support 238 can be secured to the forehead of the patient 14, such as with a dermal patch, such as those described herein, and/or can be secured to the headgear 300. For example, the optional forehead support 238 can be coupled (e.g., releasably coupled) to the top strap(s) 310 of the headgear 300. The optional forehead support 238 can be connected to the headgear 300 directly or indirectly, such as through a member than depends from the top strap(s) 310 or other portion of the headgear 300. The optional forehead support 238 can be coupled to the headgear 300 by any suitable arrangement, such as a two-part connection (e.g., hook and loop fastener), buckle, quick-release connector, or others.

With reference to FIG. 16, the side member 304 is shown. As described above, the side member 302 can be a mirror image, or a substantial mirror image, of the side member 304. Accordingly, the description of the side member 304 herein can equally apply to the side member 302 (but in a mirrored fashion) unless otherwise indicated or made clear by the context of the disclosure.

As illustrated, in some configurations, one or both of the top strap 310 and the rear strap 312 can be curved along its length. A slight radius to one or both of the straps 310, 312 can help the straps 310, 312 conform to the head of the patient 12 as applied in use. The rear strap 312 can curve downwardly from a forward end to a rearward (free) end. The top strap 310 can curve forwardly from a lower end to an upper (free) end.

As illustrated in FIG. 16, the side member 304 includes a gusset region 360 between the top strap 310 and the rear strap 312. The gusset region 360 maintains or helps maintain a desirable relative position (e.g., angle) between the top strap 310 and the rear strap 312. That is, the gusset region 360 can inhibit the straps 310, 312 from moving too close together or from moving too far apart. Such an arrangement can assist in keeping the headgear 300 (and, thus, the attachment regions 230) in a stable location on the head of the patient 12. The gusset region 360 is formed by additional material provided between the straps 310, 312 (or projections of the straps 310, 312) at a junction between the straps 310, 312. The material of the gusset region 360 is unitary with the straps 310, 312 and/or a remainder of the side member 304, but could be formed from a separate member or component that is attached to the side member 304. For example, a separate gusset 360 constructed in whole or in part from a material having greater stiffness than the material of the side member 304 could be attached to the side member 304 at the junction of the top strap 310 and the rear strap 312.

In some configurations, the headgear 300 could include an optional midline strap (e.g., similar to the midline strap 264) that extends between the top strap 310 and the rear strap 312 in the place of or in addition to the gusset region 360. In the illustrated arrangement, the rear strap 312 has a substantially constant width past the gusset region 360. However, in some configurations, the rear strap 312 could increase in width toward the free end or the rear portion of the headgear 300 as assembled and used. Such an increase in width could be similar to the central section 262 of the headgear 200. In such an arrangement, the several strap portions of the central section of each side member 302, 304 could each be connected to one another by a buckle (e.g., buckle 314). Alternatively, a central section could be provided as a single structure that located intermediate the side members 302, 304.

In the illustrated arrangement, the headgear 300 or the side member 304 in particular includes a front strap portion or front strap 370 that extends in a forward and/or downward direction from the junction between the top strap 310 and the rear strap 312 in use. The headgear 300 or the side member 304 in particular includes an attachment region 230, which may be or include an attachment section. In the illustrated arrangement, the attachment section is embodied by an attachment tab 232, which can be the same or substantially the same as the attachment tab 232 described above with respect to the headgear 200. The attachment tab 232 can extend at an angle 380 relative to the front strap 370 or an adjacent portion of the headgear 300 such that the attachment tab 232 and the front strap 370 or adjacent portion do not form a straight line. The angle 380 can be selected to position the attachment tab 232 in a desirable orientation relative to the patient 12, which can be the same or a similar orientation as the first patches 112 and/or the side arms 102 of the patient interface 14 in use, such as the orientation shown in FIGS. 2, 3, 5-7 and 11-13, for example.

In some configurations, the attachment tab 232 is oriented in use to extend forward enough onto the cheek or cheek region of the patient 12 to properly support the patient interface 14 and to also avoid the eye of the patient 12. In some configurations, the attachment tab 232 is angled in a downward direction in rearward-to-forward direction such that a rearward end of the attachment tab 232 is higher than a forward end. Stated another way, the forward end of the attachment tab 232 can be lower on the face of the patient 12 than the rearward end. In some configurations, the attachment tab 232 is configured to at least somewhat conform to the face (e.g., cheek or cheek region). In some configurations, the attachment tab 232 can extend inwardly toward a midline of the patient 12 in use. In other words, the attachment tabs 232 of the headgear 300 can converge in a rearward-to-forward direction. In some configurations, the attachment tabs 232 can be curved along one or more axes to have a non-planar shape (e.g., concave facing the patient 12), which may better conform to the face of the patient 12. In some configurations, it is desirable for the attachment tabs 232 to avoid a jaw region and/or a nose region of the patient 12 in use.

In some configurations, the angle 380 can be between about 110-160 degrees. Such a range of angles can allow the attachment tab 232 to be properly positioned relative to a front strap 370 or adjacent portion of the headgear 300 that passes above and/or in front of the ear of the patient 12. For example, as illustrated, the strap 220 of the headgear 200 is oriented generally in a vertical direction with the patient's 12 head upright. With such an arrangement, the angle 380 may be on a lower end of the range, or may be lower than 110 degrees in some circumstances. As illustrated, the front strap 370 is oriented to extend downwardly in front of the ear of the patient 12 with a rearward end of the front strap 370 higher and rearward of a forward end of the strap 370. With such an arrangement, the angle 380 may be closer to the middle or the higher end of the range, or could be higher than 160 degrees in some circumstances. Furthermore, the illustrated headgear 300 is useful for an infant or child interface. The angle 380 and/or other proportions of the headgear 300 (or headgear 200) could vary in an adult version.

As described above, the attachment region 230 is configured for attachment of the patient interface 14. The attachment region 230 can be located wholly on the attachment tab 232. In other configurations, the attachment region can be wholly located on the front strap 370. However, in the illustrated arrangement, the attachment region 230 is located partially on the attachment tab 232 and partially on the front strap 370 or a portion of the headgear 300 adjacent the attachment tab 232. For example, the attachment region 230 can include a fastener or connector 390, which is configured to connect directly or indirectly to the patient interface 14. The illustrated connector 390 extends along both the attachment tab 232 and the front strap 370 or portion of the headgear 300 adjacent the attachment tab 232.

In some configurations, the connector 390 is one part of a two-part connection that is complementary to the patch 118 of the patient interface 14, as shown in FIGS. 2-4. That is, the connector 390 may function in a manner similar to the first patch 112. The portion of the two-part connection, which can for example be a hook portion of a hook and loop fastener, can be permanently attached to the attachment tab 232 of the front portion 210, such as by an over-molding operation. However, other suitable methods of attachment can also be used, such as a sewn connection, for example. In addition, as described herein, other types of two-part connections can also be used.

The headgear 300 can be constructed of any suitable material or combination of materials. In some configurations, the side members 302, 304 have a degree of stretch that is less than the degree of stretch of the chinstrap 320, similar to the headgear 200. In some configurations, the chinstrap 320 is a stretch component. The chinstrap 320 can have a degree of stretch that is equal to or greater than any other portion of the headgear 300 or at least any major structural portion of the headgear 300. The side members 302, 304 or other portions of the headgear 300 beside the chinstrap 320 can be substantially non-stretch. As described above in connection with the headgear 200, it can be desirable to maintain the attachment regions 230 in a stable location on the face of the patient 12 so the patient interface 14 can be maintained in a stable location. For sealing interfaces, such an arrangement can maintain a seal between the interface 14 and the patient 12. For non-sealing interfaces, such an arrangement can maintain the interface 14 in a proper position, such as maintaining non-sealing cannula prongs within the nares of the patient 12. In some configurations, the side members 302, 304 are constructed in whole or in part from a fabric material. In some configurations, the material can be a foam and fabric composite, such as the foam and fabric composite sold under the trade name BREATH-O-PRENE. The chinstrap 320 can be constructed from an elastic material, such as a fabric material that is or contains elastic materials.

CONCLUSION

It should be emphasized that many variations and modifications may be made to the herein-described embodiments, the elements of which are to be understood as being among other acceptable examples. For example, although the present headgear includes a chinstrap, the headgear could be used without the chinstrap or could be modified for use without the chinstrap. This and all other such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. Itis to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A headgear for a respiratory interface, comprising:

a front portion comprising at least one strap, the at least one strap configured to be positioned in an anterior region of a patient's head, the front portion configured to extend from a first lateral side to a second lateral side of the patient's head;

a rear portion configured to extend around a posterior region of the patient's head from the first lateral side to the second lateral side of the patient's head, the rear portion comprising:

a central section; and a side strap extending from the central section and configured to attach to the front portion;

a midline strap configured to extend from the rear portion over a top of the patient's head in a forward-rearward direction and attach to the front portion, the midline strap being unitary with the rear portion;

a junction between the midline strap and the rear portion, the junction comprising:

a first notch at a first side of the junction; and a second notch at a second side of the junction, the second side being opposite from the first side, wherein each of the first notch and the second notch comprises:

a first portion extending inwardly at an end of the midline strap to locally reduce a width of the end of the midline strap; and a second portion extending into the rear portion.

2. The headgear of claim 1, wherein the front portion and/or the rear portion are substantially non-stretch.

3. The headgear of claim 1, further comprising a chin strap having a degree of stretch sufficient to allow a user to open his or her mouth.

4. The headgear of claim 1, wherein the front portion is flexible in torsion.

5. The headgear of claim 1, wherein a length of the front portion is adjustable.

6. The headgear of claim 1, wherein the at least one strap of the front portion comprises a first strap portion and a second strap portion configured to connect to one another along an overlapping portion, wherein a length of the overlapping portion is variable to permit adjustment of the length of the front portion.

7. The headgear of claim 6, wherein the first strap portion comprises an opening and the second strap portion passes through the opening.

8. The headgear of claim 6, wherein each of the first strap portion and the second strap portion comprises a buckle, wherein each of a first end and a second end of the rear portion passes through a respective one of the buckles, folds back on itself and attaches to itself.

9. The headgear of claim 1, wherein a length of the rear portion is adjustable.

10. The headgear of claim 1, wherein the rear portion comprises an increased width central portion having a pattern of cutouts.

11. The headgear of claim 10, wherein the pattern of cutouts of the increased width central portion defines a first ellipse and a second ellipse within the first ellipse.

12. The headgear of claim 1, further comprising an attachment region configured to support the respiratory interface, wherein the attachment region comprises a first part of a releasable connection that is configured to connect to a second part of the releasable connection on the respiratory interface, wherein the releasable connection comprises one or more of: a hook and loop fastener, a magnetic fastener, a post and aperture connection, a releasable adhesive, or an interlocking buckle or clip.

13. The headgear of claim 12, wherein the attachment region comprises a first portion and a second portion, wherein the first portion and the second portion define an angle therebetween.

14. The headgear of claim 13, wherein the angle is between about 110-160 degrees.

15. The headgear of claim 13, wherein the second portion comprises an attachment tab.

16. The headgear of claim 13, wherein the second portion is configured to be located on a cheek region of the patient in use.

17. The headgear of claim 1, wherein:

an upper edge of the central section extends in opposite lateral directions from the midline strap at the junction;

wherein the first notch extends inwardly at an intersection of the upper edge of the central section and the midline strap at the first side of the junction; and wherein the second notch extends inwardly at an intersection of the upper edge of the central section and the midline strap at the second side of the junction.

18. A patient interface assembly, comprising:

a patient interface configured to deliver breathing gases to an airway of a patient;

a headgear configured to support the patient interface, comprising:

a front portion comprising at least one strap, the at least one strap configured to be positioned in an anterior region of a patient's head, the front portion configured to extend from a first lateral side to a second lateral side of the patient's head;

a rear portion configured to extend around a posterior region of the patient's head from the first lateral side to the second lateral side of the patient's head, the rear portion comprising:

a central section; and a side strap extending from the central section and configured to attach to the front portion;

a midline strap configured to extend from the rear portion over a top of the patient's head in a forward-rearward direction and attach to the front portion, the midline strap being unitary with the rear portion;

a junction between the midline strap and the rear portion, the junction comprising:

a first notch at a first side of the junction; and a second notch at a second side of the junction, wherein the second side is located opposite from the first side;

an interface securement system; and a two-part connection; wherein a first part of the two-part connection is located on the front portion and a second part of the two-part connection is located on the patient interface; and wherein each of the first notch and the second notch comprises:

a first portion extending inwardly at an end of the midline strap to locally reduce a width of the end of the midline strap; and a second portion extending into the rear portion.

19. The patient interface assembly of claim 18, wherein the patient interface is a sealing interface configured to contact and create a seal with a face of the patient.

20. The patient interface assembly of claim 18, wherein the patient interface is a mask or a cannula.

* * * * *